(12) United States Patent
Millard et al.

(10) Patent No.: US 10,377,687 B2
(45) Date of Patent: Aug. 13, 2019

(54) PROCESSES FOR FORMING TITANIUM CATECHOL COMPLEXES

(71) Applicant: LOCKHEED MARTIN ADVANCED ENERGY STORAGE, LLC, Bethesda, MD (US)

(72) Inventors: Matthew Millard, Cambridge, MA (US); John Goeltz, Carmel, CA (US)

(73) Assignee: Lockheed Martin Energy, LLC, Bethesda, MD (US)

( * ) Notice: Subject to any disclaimer, the term of this patent is extended or adjusted under 35 U.S.C. 154(b) by 265 days.

(21) Appl. No.: 15/436,716

(22) Filed: Feb. 17, 2017

(65) Prior Publication Data

US 2018/0029966 A1   Feb. 1, 2018

Related U.S. Application Data

(63) Continuation-in-part of application No. 15/220,322, filed on Jul. 26, 2016.
(Continued)

(51) Int. Cl.
| | |
|---|---|
| C07C 37/66 | (2006.01) |
| H01M 8/18 | (2006.01) |
| C07F 7/28 | (2006.01) |

(52) U.S. Cl.
CPC .............. C07C 37/66 (2013.01); C07F 7/28 (2013.01); H01M 8/188 (2013.01)

(58) Field of Classification Search
CPC ........... C07C 37/66; C07F 7/28; H01M 8/188
See application file for complete search history.

(56) References Cited

U.S. PATENT DOCUMENTS

| | | |
|---|---|---|
| 1,279,295 A | 9/1918 | Downs |
| 2,353,782 A | 7/1944 | Neumark |
| | (Continued) | |

FOREIGN PATENT DOCUMENTS

| | | |
|---|---|---|
| CN | 1284208 A | 2/2001 |
| CN | 101877412 A | 11/2010 |
| | (Continued) | |

OTHER PUBLICATIONS

Abdulghani et al., "Preparation and Characterization of Di-, Tri-, and Tetranuclear Schiff Base Complexes Derived from Diamines and 3,4-Dihydroxybenzaldehyde," Hindawi Publishing Corp, Bioinorganic Chemistry and Applications, 2013, pp. 1-14.
(Continued)

Primary Examiner — Helen Oi K Conley
(74) Attorney, Agent, or Firm — BakerHostetler

(57) ABSTRACT

Titanium complexes containing at least one catecholate ligand can be desirable active materials for flow batteries and other electrochemical energy storage systems. Such complexes can be formed through reacting a catechol compound with a titanium reagent in an organic solvent, removing a byproduct species, and then obtaining an aqueous phase containing a salt form of the titanium catechol complex, particularly an alkali metal salt form. More specifically, the methods can include: forming a catechol solution containing a catechol compound and an organic solvent, contacting a titanium reagent with the catechol solution to form a reaction mixture, reacting the titanium reagent with the catechol compound to form an intermediate titanium catechol complex and a byproduct species, separating the byproduct species, and combining an alkaline aqueous solution containing a base with the intermediate titanium catechol complex to produce a salt form titanium catechol complex at least partially dissolved in an aqueous phase.

23 Claims, 6 Drawing Sheets

Related U.S. Application Data

(60) Provisional application No. 62/441,146, filed on Dec. 30, 2016, provisional application No. 62/441,149, filed on Dec. 30, 2016, provisional application No. 62/441,150, filed on Dec. 30, 2016, provisional application No. 62/441,151, filed on Dec. 30, 2016, provisional application No. 62/441,153, filed on Dec. 30, 2016, provisional application No. 62/441,154, filed on Dec. 30, 2016.

(56) References Cited

U.S. PATENT DOCUMENTS

| | | | |
|---|---|---|---|
| 2,415,792 | A | 2/1947 | Gravell |
| 3,294,588 | A | 12/1966 | Morton |
| 3,425,796 | A | 2/1969 | Bauer |
| 3,428,654 | A | 2/1969 | Rubinfeld |
| 3,573,984 | A | 4/1971 | Shah |
| 3,707,449 | A | 12/1972 | Reinhardt et al. |
| 3,772,379 | A | 11/1973 | Woodgate |
| 3,801,642 | A | 4/1974 | Worrel |
| 3,876,435 | A | 4/1975 | Dollman |
| 3,916,004 | A | 10/1975 | Okada et al. |
| 3,919,000 | A | 11/1975 | Yarrington |
| 3,920,756 | A | 11/1975 | Tahara et al. |
| 3,929,506 | A | 12/1975 | Leddy et al. |
| 3,985,517 | A | 10/1976 | Johnson |
| 3,985,585 | A | 10/1976 | Tuttle et al. |
| 4,046,861 | A | 9/1977 | Reinhardt et al. |
| 4,064,324 | A | 12/1977 | Eustace |
| 4,069,371 | A | 1/1978 | Zito |
| 4,126,529 | A | 11/1978 | DeBerry |
| 4,180,623 | A | 12/1979 | Adams |
| 4,202,799 | A | 5/1980 | Yoshimura et al. |
| 4,233,144 | A | 11/1980 | Pace et al. |
| 4,362,791 | A | 12/1982 | Kaneko et al. |
| 4,378,995 | A | 4/1983 | Gratzfeld et al. |
| 4,410,606 | A | 10/1983 | Loutfy et al. |
| 4,436,711 | A | 3/1984 | Olson |
| 4,436,712 | A | 3/1984 | Olson |
| 4,436,713 | A | 3/1984 | Olson |
| 4,436,714 | A | 3/1984 | Olson |
| 4,443,423 | A | 4/1984 | Olson |
| 4,443,424 | A | 4/1984 | Olson |
| 4,468,441 | A | 8/1984 | D'Agostino et al. |
| 4,485,154 | A | 11/1984 | Remick et al. |
| 4,520,083 | A | 5/1985 | Prater et al. |
| 4,563,403 | A | 1/1986 | Julian |
| 4,592,973 | A | 6/1986 | Pemsler et al. |
| 4,617,244 | A | 10/1986 | Greene |
| 4,680,308 | A | 7/1987 | Schwartz et al. |
| 4,818,646 | A | 4/1989 | Takakubo et al. |
| 4,880,758 | A | 11/1989 | Heistand, II et al. |
| 4,952,289 | A | 8/1990 | Ciccone et al. |
| 4,959,135 | A | 9/1990 | Zenner et al. |
| 4,973,720 | A | 11/1990 | Saito et al. |
| 5,084,533 | A | 1/1992 | Shah et al. |
| 5,102,906 | A | 4/1992 | Nakayama et al. |
| 5,122,461 | A | 6/1992 | Hsiung et al. |
| 5,264,097 | A | 11/1993 | Vaughan |
| 5,302,481 | A | 4/1994 | Ong |
| 5,318,865 | A | 6/1994 | Kaneko et al. |
| 5,433,934 | A | 7/1995 | Chang et al. |
| 5,472,807 | A | 12/1995 | Licht et al. |
| 5,643,670 | A | 7/1997 | Chung |
| 5,679,239 | A | 10/1997 | Blum et al. |
| 5,759,711 | A | 6/1998 | Miyabayashi et al. |
| 5,785,841 | A | 7/1998 | Tseng |
| 5,876,581 | A | 3/1999 | Itaya et al. |
| 5,910,366 | A | 6/1999 | Chowdhury et al. |
| 6,001,326 | A | 12/1999 | Kim et al. |
| 6,030,517 | A | 2/2000 | Lincot et al. |
| 6,054,230 | A | 4/2000 | Kato |
| 6,461,772 | B1 | 10/2002 | Miyake et al. |
| 6,475,661 | B1 | 11/2002 | Pellegri et al. |
| 6,485,868 | B1 | 11/2002 | Tsujioka et al. |
| 6,555,989 | B1 | 4/2003 | Pearson |
| 6,585,951 | B1 | 7/2003 | Hong et al. |
| 6,624,328 | B1 | 9/2003 | Guerra |
| 7,046,418 | B2 | 5/2006 | Lin et al. |
| 7,193,764 | B2 | 3/2007 | Lin et al. |
| 7,223,833 | B1 | 5/2007 | Nielsen et al. |
| 7,252,905 | B2 | 8/2007 | Clarke et al. |
| 7,265,162 | B2 | 9/2007 | Yandrasits et al. |
| 7,348,088 | B2 | 3/2008 | Hamrock et al. |
| 7,463,917 | B2 | 12/2008 | Martinez |
| 7,508,568 | B2 | 3/2009 | Lin et al. |
| 7,550,231 | B2 | 6/2009 | Stauffer |
| 7,557,164 | B2 | 7/2009 | Felix et al. |
| 7,625,663 | B2 | 12/2009 | Clarke et al. |
| 7,645,540 | B2 | 1/2010 | Boone et al. |
| 7,678,728 | B2 | 3/2010 | Olson et al. |
| 7,745,056 | B2 | 6/2010 | Lee et al. |
| 7,767,777 | B2 | 8/2010 | Buesing et al. |
| 7,927,731 | B2 | 4/2011 | Sahu |
| 7,931,981 | B2 | 4/2011 | Boone et al. |
| 7,935,366 | B2 | 5/2011 | Pahuja et al. |
| 7,998,335 | B2 | 8/2011 | Feeney et al. |
| 8,129,554 | B2 | 3/2012 | Schwaiger |
| 8,187,441 | B2 | 5/2012 | Evans et al. |
| 8,445,118 | B2 | 5/2013 | Cordonier et al. |
| 8,492,581 | B2 | 7/2013 | Frost et al. |
| 8,691,413 | B2 | 4/2014 | Esswein et al. |
| 8,753,761 | B2 | 6/2014 | Esswein et al. |
| 9,300,000 | B2 | 3/2016 | Jansen et al. |
| 9,382,274 | B2 | 7/2016 | Esswein et al. |
| 9,409,842 | B1 | 8/2016 | Fu et al. |
| 2002/0177042 | A1 | 11/2002 | Amendola |
| 2003/0068561 | A1 | 4/2003 | Okahara et al. |
| 2003/0143456 | A1 | 7/2003 | Kazacos et al. |
| 2003/0228394 | A1 | 12/2003 | Abdel-Monem et al. |
| 2004/0096746 | A1 | 5/2004 | Wietelmann et al. |
| 2005/0098437 | A1 | 5/2005 | Shiepe |
| 2005/0244707 | A1 | 11/2005 | Skyllas-Kazacos et al. |
| 2006/0047094 | A1 | 3/2006 | Cherkasov et al. |
| 2007/0275291 | A1 | 11/2007 | Gu et al. |
| 2008/0274385 | A1 | 11/2008 | Creeth |
| 2008/0292964 | A1 | 11/2008 | Kazacos et al. |
| 2009/0110998 | A1 | 4/2009 | Miyachi et al. |
| 2009/0130525 | A1 | 5/2009 | Miyachi et al. |
| 2009/0208807 | A1 | 8/2009 | Miyachi et al. |
| 2009/0308752 | A1 | 12/2009 | Evans et al. |
| 2010/0003586 | A1 | 1/2010 | Sahu |
| 2010/0059388 | A1 | 3/2010 | Clarke et al. |
| 2010/0086823 | A1 | 4/2010 | Koshino et al. |
| 2010/0086983 | A1 | 4/2010 | Gellett et al. |
| 2010/0239946 | A1 | 9/2010 | Miyachi et al. |
| 2011/0014532 | A1 | 1/2011 | Knuckey et al. |
| 2011/0136016 | A1 | 6/2011 | Huang et al. |
| 2011/0189549 | A1 | 8/2011 | Sun et al. |
| 2011/0195283 | A1 | 8/2011 | Sun et al. |
| 2011/0200890 | A1 | 8/2011 | Kocherginsky |
| 2011/0223450 | A1 | 9/2011 | Horne et al. |
| 2011/0244277 | A1 | 10/2011 | Gordon, II et al. |
| 2011/0244367 | A1 | 10/2011 | Watahiki et al. |
| 2012/0052347 | A1 | 3/2012 | Wilson et al. |
| 2012/0077095 | A1 | 3/2012 | Roumi et al. |
| 2012/0107661 | A1 | 5/2012 | Lee et al. |
| 2012/0135278 | A1 | 5/2012 | Yoshie et al. |
| 2012/0171541 | A1 | 7/2012 | Park et al. |
| 2012/0183868 | A1 | 7/2012 | Toussaint et al. |
| 2012/0196188 | A1 | 8/2012 | Zhang et al. |
| 2012/0202099 | A1 | 8/2012 | Perry et al. |
| 2012/0208061 | A1 | 8/2012 | Sahu et al. |
| 2012/0244406 | A1 | 9/2012 | Xia et al. |
| 2012/0263990 | A1 | 10/2012 | Kim |
| 2013/0004819 | A1 | 1/2013 | Mun et al. |
| 2013/0157087 | A1 | 6/2013 | Pandy et al. |
| 2013/0252062 | A1 | 9/2013 | Wilkins et al. |
| 2013/0252137 | A1 | 9/2013 | Zhang et al. |
| 2014/0028260 | A1 | 1/2014 | Goeltz et al. |
| 2014/0028261 | A1 | 1/2014 | Esswein et al. |
| 2014/0030572 | A1 | 1/2014 | Esswein et al. |
| 2014/0030573 | A1 | 1/2014 | Esswein et al. |

(56) References Cited

U.S. PATENT DOCUMENTS

| | | |
|---|---|---|
| 2014/0030631 A1 | 1/2014 | Esswein et al. |
| 2014/0051003 A1 | 2/2014 | Esswein et al. |
| 2014/0080035 A1 | 3/2014 | Esswein et al. |
| 2014/0138576 A1 | 5/2014 | Esswein et al. |
| 2014/0178735 A1 | 6/2014 | Wang et al. |
| 2014/0193687 A1 | 7/2014 | Park et al. |
| 2014/0239906 A1 | 8/2014 | Anderson et al. |
| 2014/0274936 A1 | 9/2014 | Piccariello et al. |
| 2014/0349177 A1 | 11/2014 | Chung et al. |
| 2014/0377666 A1 | 12/2014 | Kodama et al. |
| 2015/0236543 A1 | 8/2015 | Brushett et al. |
| 2015/0372333 A1 | 12/2015 | Odom et al. |
| 2016/0066578 A1 | 3/2016 | Ala'Aldeen et al. |
| 2016/0149251 A1 | 5/2016 | Reece |
| 2016/0208165 A1 | 7/2016 | Li et al. |
| 2016/0264603 A1 | 9/2016 | Esswein et al. |
| 2016/0268623 A1 | 9/2016 | Esswein et al. |
| 2016/0272659 A1 | 9/2016 | King et al. |
| 2016/0276693 A1 | 9/2016 | Goeltz et al. |
| 2016/0276694 A1 | 9/2016 | Goeltz et al. |
| 2016/0276695 A1 | 9/2016 | Esswein et al. |
| 2017/0253620 A1 | 9/2017 | Humbarger et al. |
| 2017/0256811 A1 | 9/2017 | Humbarger et al. |
| 2017/0271704 A1 | 9/2017 | Morris-Cohen |

FOREIGN PATENT DOCUMENTS

| | | |
|---|---|---|
| EP | 0814527 A2 | 12/1997 |
| EP | 1290068 A2 | 3/2003 |
| EP | 1411576 A1 | 4/2004 |
| EP | 1901379 A1 | 3/2008 |
| EP | 2235781 A1 | 10/2010 |
| EP | 2463950 A1 | 6/2012 |
| FR | 1533662 A | 7/1968 |
| GB | 1354886 A | 6/1974 |
| WO | WO-95/12219 A1 | 5/1995 |
| WO | WO-1997/017354 A1 | 5/1997 |
| WO | WO-2004/095602 A2 | 11/2004 |
| WO | WO-2006/135958 A1 | 12/2006 |
| WO | WO-2007/044852 A2 | 4/2007 |
| WO | WO-2007/101284 A1 | 9/2007 |
| WO | WO-2011/075135 A1 | 6/2011 |
| WO | WO-2011/098781 A1 | 8/2011 |
| WO | WO-2011/149624 A1 | 12/2011 |
| WO | WO-2012/075810 A1 | 6/2012 |
| WO | WO-2013/006427 A1 | 1/2013 |
| WO | WO-2013/048603 A1 | 4/2013 |
| WO | WO 2014-018593 A1 | 1/2014 |
| WO | WO-2015/069439 A1 | 5/2015 |

OTHER PUBLICATIONS

IUPAC Compendium of Chemical Terminology, "coordinatively unsaturated complex," 1997, http://old.iupac.org/goldbook/C01334.pdf.

Mansoor, "Mixed Metal Complexes of Copper (II), Nickel (II) and Zinc (II) Involving Dopa and Dopamine," International Journal of ChemTech Research, Jan.-Mar. 2010, vol. 2, No. 1, pp. 640-645.

International Search Report and Written Opinion from PCT/US17/14764, dated Apr. 20, 2017.

International Search Report and Written Opinion from PCT/US16/69190, dated May 3, 2017.

International Search Report and Written Opinion from PCT/US2017/022203, dated Jun. 6, 2017.

Ahluwalia et al., Intermediates for Organic Synthesis, Chapter 1, Phenols, Sections 1.21 and 1.23, (2003), I.K. International Pvt. Ltd.

Ahn et al., "A Study of Benzene 1,2,4-Trisphosphate Derivatives as Inositol 1,4,5-Trisphosphate 3-Kinase Inhibitors," Bull. Korean Chem. Soc., 2002, pp. 515-517, vol. 23., No. 3.

Borgias, "Synthetic, structural, and physical studies of titanium complexes of catechol and 3,5-di-tert-butylcatechol," Inorg. Chem., Apr. 1984, 23(8), 1009-1016.

Bosch et al., "Novel Catalysis of Hydroquinone Autoxidation with Nitrogen Oxides," J. Org. Chem., 1994, pp. 2529-2536, 59.

Brezina, "Study of the reduction of oxygen on a carbon paste electrode in an alkaline medium," Coll. Czech. Chem. Commun., 1973, 38(10), 3024-3031.

Caulton, "Systematics and Future Projections Concerning Redox-Noninnocent Amide/Imine Ligands," Eur. J. Inorg. Chem., Jan. 2012, 2012(3), 435-443.

Cerofontain et al. "Sulfonation and sulfation on reaction of 1,2-dihydroxybenzene and its methyl ethers in concentrated aqueous sulfuric acid," Recl Tray Chim Pays-Bas, 1988, pp. 325-330, vol. 107.

Chen, "Solution Redox Couples for Electrochemical Energy Storage: I. Iron (III)-Iron (II) Complexes with O-Phenanthroline and Related Ligands," Journal of the Electrochemical Society, Jul. 1981, 128(7), 1460-1467.

Cohen, "The Association of Ferrocyanide Ions With Various Cations," J. Phys. Chem., Aug. 1957, 61(8), 1096-1100.

Davies, "Eiectroceramics from Source Materials via Molecular Intermediates: PbTi03 from Ti02 via [Ti(catecholate)3]2—," J. Am. Ceram. Soc., Aug. 1990, 73(8), 2570-2572.

Davies, "Electroceramics from Source Materials via Molecular Intermediates: BaTl03 from Tl02 via [Tl(catecholate)3]2—," May 1990, J. Am. Ceram. Soc., Aug. 1990, 73(5), 1429-30.

Dehaen et al, "A Self-Assembled Complex with a Titanium (IV) Catecholate Core as a Potential Bimodal Contrast Agent," Chem Eur J, 2012, pp. 293-302, vol. 18.

Fryda, "Wastewater Treatment With Diamond Electrodes," Diamond Materials, Electrochemical Society Proceedings, 2000, 99(32), 473-483.

Gail, "Cyano Compounds, Inorganic" in Ullmann's Encyclopedia of Industrial Chemistry, 2012, 10, 674-710.

Hollandsworth, "Zinc/Ferrocyanide Battery Development Phase IV" Lockheed Missiles and Space Company, Inc., Contractor report, Sandia Contract DE-AC04-76DP00789, May 1985, 278 pages.

Kim, "Novel catalytic effects of Mn3O4 for all vanadium redox flow batteries," Chem. Commun., Apr. 2012, 48(44), 5455-5457.

Kulesza, "Electrochemical preparation and characterization of hybrid films composed of Prussian blue type metal hexacyanoferrate and conducting polymer," Electrochimica Acta, Aug. 2001, 46(26-27), 4065-4073.

Lang et al., "Studies on the Biosynthesis of Bovilactone-4,4 and Related Fungal Meroterpenoids," Eur. J. Org. Chem., 2008, pp. 3544-3551.

Lang et al., "Studies on the Structure and Biosynthesis of Tridentoquinone and Related Meroterpenoids from the Mushroom *Suillus tridentinus* (Boletales)," Eur. J. Org. Chem., 2008, pp. 816-825.

Leung, "An undivided zinc—cerium redox flow battery operating at room temperature (295 K)," Electrochemistry Communications, 2011, vol. 13, pp. 770-773.

Leung, "Ce(III)/Ce(iV) in methanesulfonic acid as the positive half cell of a redox flow battery," Electrochimica Acta, 2011, vol. 56, pp. 2145-2153.

Leung, "Characterization of a zinc—cerium flow battery," Journal of Power Sources, 2011, vol. 195, pp. 5174-5185.

Leung, "Development of a Zinc—Cerium Redox Flow Battery", 2011, 352 pages.

Leung, "Zinc deposition and dissolution in methanesulfonic acid onto a carbon composite electrode as the negative electrode reactions in a hybrid redox flow battery," Electrochimica Acta, 2011, vol. 56, pp. 6536-6546.

Maison, et al., "Effect of Calcination Temperature on Phase Transformation and Particle size of Barium Titanate Fine Powders Synthesized by the Catecholate Process," ScienceAsia, 2001, pp. 239-243, 27.

McOmie et al. "The Thiele-Winter Acetoxylation of Quinones," Organic Reactions, 1972, pp. 199-277, 19, John Wiley and Sons, Inc., New York.

Modiba, "Electrochemical impedance spectroscopy study of Ce(IV) with aminopolycarboxylate ligands for redox flow batteries applications," Journal of Power Sources, May 2012, vol. 205, 1-9.

(56) References Cited

OTHER PUBLICATIONS

Modiba, "Electrochemical study of cerium(IV) in the presence of ethylenediaminetetraacetic acid (EDTA) and diethylenetriaminepentaacetate (DTPA) ligands," Journal of Applied Electrochemistry, Sep. 2008, 38(9), 1293-1299.
Modiba, "Electrolytes for redox flow battery systems," Dissertation presented for the degree of Doctor of Philosophy Chemistry at the University of Stellenbosch, Department of Chemistry and Polymer Science, Mar. 2010.
Murakami et al., "The Chelating Behavior of Catechol-4-sulfonate with Iron(III) Ion," Bulletin of the Chemical Society of Japan, 1963, pp. 1408-1411; vol. 36.
Nguyen, "Flow Batteries," The Electrochemical Society Interface, Fall2010, 19(3), 54-56.
Pharr, "Infrared Spectroelectrochemical Analysis of Adsorbed *Hexacyanoferrate* Species Formed during Potential Cycling in the Ferrocyanide/Ferricyanide Redox Couple," Anal. Chem., Nov. 1997, 69(22), 4673-4679.
Raymond, "Coordination isomers of biological iron transport compounds. VI. Models of the enterobactin coordination site. A crystal field effect in the structure of potassium tris( catecholato)chromate( III) and -ferrate( III) sesq u ihyd rates, K3[M( 02C6H4 )3]. 1 . 5H20, M=chromium, iron," J. Am. Chem. Soc., Mar. 1976, 98(7), 1767-1774.
Saito et al. "DPPH radical-scavenging reaction of protocatechuic acid: differnce in reactivity between acids and their esters," Helv Chim Acta, 2006, pp. 1395-1407, vol. 89.
Sever et al, "Visible absorption spectra of metal-catecholate and metal-tironate complexes," Dalton Trans., pp. 1061-1072, 2004.
SIGMA-ALDRICH Tris(hydroxymethyl)aminomethane, 2015.
Soloveichik, "Flow Batteries: Current Status and Trends," 2015, Chem. Rev., 115 (20), pp. 11533-11558.
Sommer, "Titanium (IV) complexes with ligands having oxygen donor atoms in aqueous solutions," Zeitschrift fur Anorganische and Aligemeine Chemie, Mar. 1963, pp. 191-197, vol. 321, issue 3-4.
Spyroudis, "Hydroxyquinones: Synthesis and Reactivity," Molecules, 2000, pp. 1291-1330, 5.

Steenken, "One-electron redox potentials of phenols. Hydroxy- and aminophenols and related compounds of biological interest," J. Phys. Chem., Sep. 1982, 86(18), 3661-3667.
Torres-Gomez, "Energy Storage in Hybrid Organic-Inorganic Materials Hexacyanoferrate-Doped Polypyrrole as Cathode in Reversible Lithium Cells," J. of the Electrochemical Society, 2000, 147(7), 2513-2516.
Trant, "Solubility of Sodium Ferrocyanide and Potassium Ferrocyanide in Solutions of NaOH and KOH Mixtures at 25.degree. C," University of Rochester, The David T. Kearns Center, Xerox Undergraduate Research Fellows Program, Jul. 28, 2011, 1 page.
Vercillo, "Solubility of Sodium Ferrocyanide in Sodium Hydroxide and Potassium Ferrocyanide in Potassium Hydroxide," University of Rochester, The David T. Kearns Center, Xerox Undergraduate Research Fellows Program, Jul. 28, 2011, 1 page.
Wang, "Determination of iron, titanium, osmium, and aluminum with tiron by reversephase high performance liquid chromatography/electrochemistry," Microchem. J., Jun. 1991, 43(3), 191-197.
Weber, "Redox flow batteries: a review," Journal of Applied Electrochemistry, Oct. 2011, 41(10), 1137-1164.
Westervelt, "A Study of the Calcium Complex of the Potassium Salt of Catechol-4-Sulfonate in Aqueous, Alkalino Media," Jan. 1981, Doctoral Dissertation, retrieved from https://smartech.gatech.edu/bitstream/handle/1853/5723/westervelt-iii_hh.pdf.
Ali et al., "Synthesis and Processing Characteristics of $Ba_{0.65}Sr_{0.35}TiO_3$ Powders from Catecholate Precursors," J Am Ceram Soc, 1993, pp. 2321-2326, vol. 76, No. 9.
Devi et al., "pH-metric investigation on Mixed-Ligand Complexes of Ca(II), Mg(II) and Zn(II) with L-Dopa and 1,10 Phenantroline in Propylene glycol-Water Mixtures," RRJC, Oct.-Dec. 2012, vol. 1, Issue 1, pp. 13-22.
Xu, "Mechanics of metal-catecholate complexes: The roles of coordination state and metal types," Scientific Reports, Oct. 10, 2013, 3:2914, pp. 1-7.
Vliet et al., "Hydroxyhydroquinone Triacetate," Organic Synthesys, 1941, Coll vol. 1, p. 317 (1941), vol. 4, p. 35 (1925) 3 pages.
International Search Report and Written Opinion dated Jan. 19, 2017 from International Application No. PCT/US16/58433.
International Search Report and Written Opinion dated Feb. 17, 2017 from International Application No. PCT/US16/65159.
Wang et al., "Issues in Freeze Drying of Aqueous Solutions," Chinese Journal of Chemical Engineering, 2012, 20(3), pp. 551-559.

PROCESSES FOR FORMING TITANIUM CATECHOL COMPLEXES

CROSS-REFERENCE TO RELATED APPLICATIONS

The present application is a continuation-in-part of U.S. patent application Ser. No. 15/220,322, filed on Jul. 26, 2016 and incorporated by reference herein in its entirety. The present application also claims the benefit of priority under 35 U.S.C. § 119 from U.S. Provisional Patent Applications 62/441,146; 62/441,149; 62/441,150; 62/441,151; 62/441,153 and 62/441,154, each filed on Dec. 30, 2016 and incorporated herein by reference in its entirety.

STATEMENT REGARDING FEDERALLY SPONSORED RESEARCH OR DEVELOPMENT

Not applicable.

FIELD

The present disclosure generally relates to energy storage and, more specifically, to methods for preparing titanium catechol complexes as active materials for use in energy storage systems.

BACKGROUND

Electrochemical energy storage systems, such as batteries, supercapacitors and the like, have been widely proposed for large-scale energy storage applications. Various battery designs, including flow batteries, have been considered for this purpose. Compared to other types of electrochemical energy storage systems, flow batteries can be advantageous, particularly for large-scale applications, due to their ability to decouple the parameters of power density and energy density from one another.

Flow batteries generally include negative and positive active materials in corresponding electrolyte solutions, which are flowed separately across opposing sides of a membrane or separator in an electrochemical cell containing negative and positive electrodes. The flow battery is charged or discharged through electrochemical reactions of the active materials that occur inside the two half-cells. As used herein, the terms "active material," "electroactive material," "redox-active material" or variants thereof synonymously refer to materials that undergo a change in oxidation state during operation of a flow battery or like electrochemical energy storage system (i.e., during charging or discharging). Although flow batteries hold significant promise for large-scale energy storage applications, they have often been plagued by sub-optimal energy storage performance (e.g., round trip energy efficiency) and limited cycle life, among other factors. Despite significant investigational efforts, no commercially viable flow battery technologies have yet been developed.

Some active materials can be organic compounds that are capable of undergoing a reversible oxidation-reduction cycle. Organic active materials often provide relatively limited energy densities due to low solubility values, particularly in aqueous electrolyte solutions, and low electrical conductivity. To compensate for low solubility values, organic active materials are frequently used in non-aqueous electrolyte solutions so that increased solubility can be realized. High synthesis costs and environmental issues can sometimes accompany the use of organic active materials in flow batteries.

Metal-based active materials can often be desirable for use in flow batteries and other electrochemical energy storage systems. Although non-ligated metal ions (e.g., dissolved salts of a redox-active metal) can be used as an active material, it can often be more desirable to utilize coordination complexes for this purpose. As used herein, the terms "coordination complex," "coordination compound," "metal-ligand complex," or simply "complex" synonymously refer to a compound having at least one covalent bond formed between a metal center and a donor ligand. The metal center can cycle between an oxidized form and a reduced form in an electrolyte solution, where the oxidized and reduced forms of the metal center represent states of full charge or full discharge depending upon the particular half-cell in which the coordination complex is present. In certain instances, additional electrons can be transferred through the oxidation or reduction of one or more of the molecules constituting the ligands.

Titanium complexes can be particularly desirable active materials for use in flow batteries and other electrochemical energy storage systems, since such metal complexes can provide good half-cell potentials (e.g., less than −0.3 V) and current efficiencies exceeding 85% at high current density values (e.g., greater than 100 mA/cm$^2$). Various catechol complexes of titanium can be especially desirable active materials in this regard, since they are relatively stable complexes and have a significant degree of solubility in aqueous media. Although various methods are available for synthesizing catechol complexes of titanium (also referred to herein as titanium catecholate complexes or titanium catechol complexes), none are presently viable for producing the significant quantities of these complexes needed to support commercial-scale energy storage applications. In addition, concurrent production of extraneous salts during conventional syntheses of titanium catechol complexes can be especially problematic, as discussed further hereinafter.

Titanium catechol complexes are usually synthesized in a salt form, wherein the complex itself bears a formal negative charge and one or more positively charged counterions are present to maintain charge balance. Concurrent production of extraneous salts that are not associated with the titanium catechol complexes can, in many instances, undesirably decrease solubility of the complexes through a common ion effect upon forming an electrolyte solution, particularly an aqueous electrolyte solution. Introduction of excessive counterions while forming titanium catechol complexes in a desired salt form can lead to the undesirable co-production of extraneous salts. In many instances, the excessive counterions can react with a byproduct formed during the synthesis of the titanium catechol complexes and lead to production of the extraneous salts. Similarly, introduction of insufficient counterions can lead to incomplete formation of a desired salt form. Neither of these situations is optimal for forming electrolyte solutions intended to have a high energy density and other desirable parameters.

In view of the foregoing, improved methods for synthesizing titanium catechol complexes to support their use as active materials in energy storage applications would be highly desirable in the art. The present disclosure satisfies the foregoing needs and provides related advantages as well.

SUMMARY

In various embodiments, methods for synthesizing coordination complexes containing titanium are described herein. The methods can include: forming a catechol solution containing a catechol compound and an organic solvent; contacting a titanium reagent with the catechol solution to form a reaction mixture; reacting the titanium reagent with the catechol compound to form an intermediate titanium catechol complex and a byproduct species; separating the byproduct species from the intermediate titanium catechol complex; and combining an alkaline aqueous solution containing a base with the intermediate titanium catechol complex. The base converts the intermediate titanium catechol complex into a salt form titanium catechol complex that is at least partially dissolved in an aqueous phase.

In other various embodiments, methods for synthesizing coordination complexes containing titanium can include: forming a catechol solution containing a catechol compound and an organic solvent; contacting a titanium alkoxide with the catechol solution to form a reaction mixture; reacting the titanium alkoxide with the catechol compound to form an intermediate titanium catechol complex and an alcohol; and without separating the intermediate titanium catechol complex from the alcohol, combining an alkaline aqueous solution containing a base with the intermediate titanium catechol complex. The base converts the intermediate titanium catechol complex into a salt form titanium catechol complex that is at least partially dissolved in an aqueous phase that also contains the alcohol. In further embodiments, the methods can additionally include removing at least a portion of the alcohol from the aqueous phase.

The foregoing has outlined rather broadly the features of the present disclosure in order that the detailed description that follows can be better understood. Additional features and advantages of the disclosure will be described hereinafter. These and other advantages and features will become more apparent from the following description.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
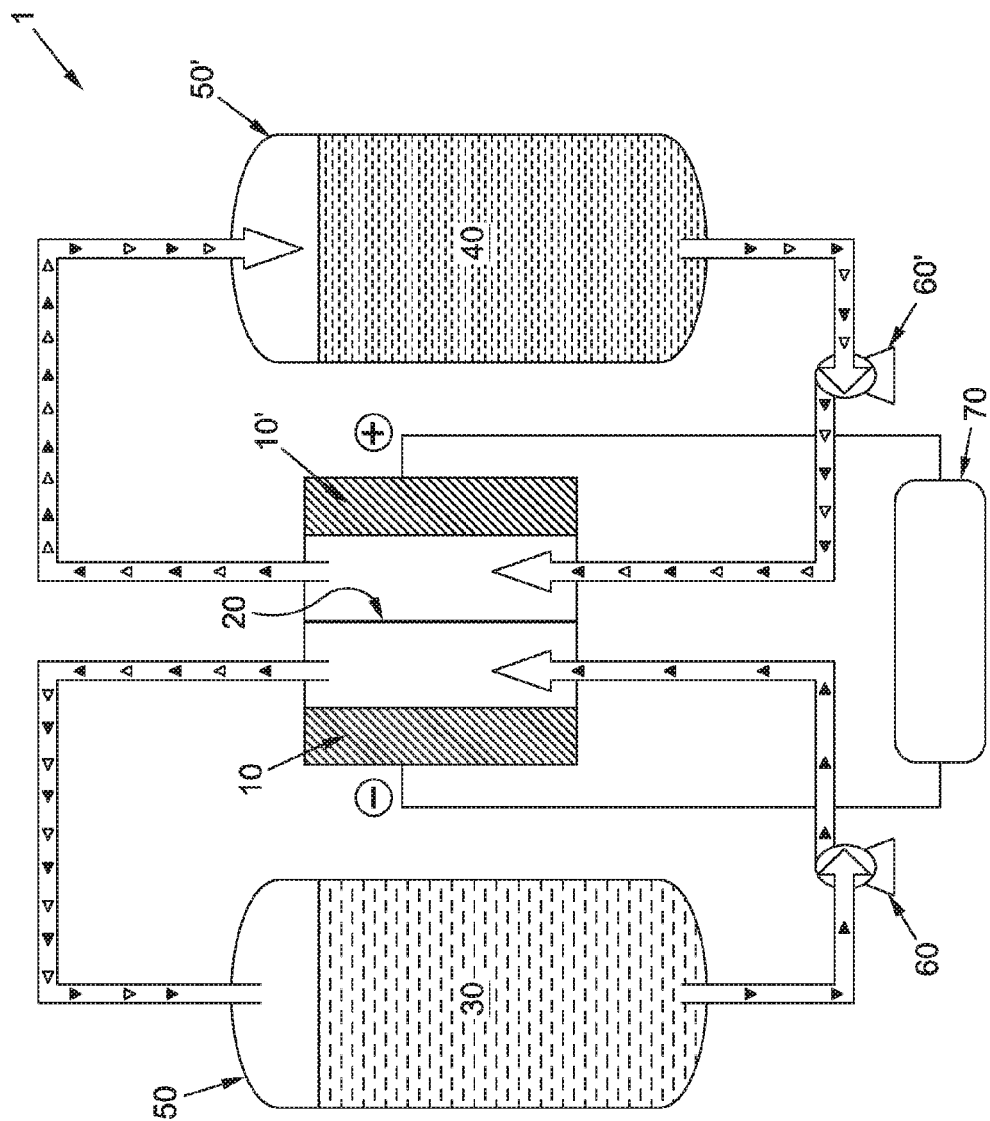
FIG. 1 shows a schematic of an illustrative flow battery.

The present disclosure is directed, in part, to flow batteries and compositions containing salt form titanium catechol complexes, particularly alkali metal salt forms, that are free or substantially free of extraneous salts or other byproducts formed during their syntheses. The present disclosure is also directed, in part, to methods for synthesizing salt form titanium catechol complexes, particularly alkali metal salt forms, that are free or substantially free of extraneous salts or other byproducts formed during their syntheses.

The present disclosure may be understood more readily by reference to the following description taken in connection with the accompanying figures and examples, all of which form a part of this disclosure. It is to be understood that this disclosure is not limited to the specific products, methods, conditions or parameters described and/or shown herein. Further, the terminology used herein is for purposes of describing particular embodiments by way of example only and is not intended to be limiting unless otherwise specified. Similarly, unless specifically stated otherwise, any description herein directed to a composition is intended to refer to both solid and liquid versions of the composition, including solutions and electrolytes containing the composition, and electrochemical cells, flow batteries, and other energy storage systems containing such solutions and electrolytes. Further, it is to be recognized that where the disclosure herein describes an electrochemical cell, flow battery, or other energy storage system, it is to be appreciated that methods for operating the electrochemical cell, flow battery, or other energy storage system are also implicitly described.

It is also to be appreciated that certain features of the present disclosure may be described herein in the context of separate embodiments for clarity purposes, but may also be provided in combination with one another in a single embodiment. That is, unless obviously incompatible or specifically excluded, each individual embodiment is deemed to be combinable with any other embodiment(s) and the combination is considered to represent another distinct embodiment. Conversely, various features of the present disclosure that are described in the context of a single embodiment for brevity's sake may also be provided separately or in any sub-combination. Finally, while a particular embodiment may be described as part of a series of steps or part of a more general structure, each step or sub-structure may also be considered an independent embodiment in itself.

Unless stated otherwise, it is to be understood that each individual element in a list and every combination of individual elements in that list is to be interpreted as a distinct embodiment. For example, a list of embodiments presented as "A, B, or C" is to be interpreted as including the embodiments "A," "B," "C," "A or B," "A or C," "B or C," or "A, B, or C."

In the present disclosure, the singular forms of the articles "a," "an," and "the" also include the corresponding plural references, and reference to a particular numerical value includes at least that particular value, unless the context clearly indicates otherwise. Thus, for example, reference to "a material" is a reference to at least one of such materials and equivalents thereof.

In general, use of the term "about" indicates approximations that can vary depending on the desired properties sought to be obtained by the disclosed subject matter and is to be interpreted in a context-dependent manner based on functionality. Accordingly, one having ordinary skill in the art will be able to interpret a degree of variance on a case-by-case basis. In some instances, the number of significant figures used when expressing a particular value may be a representative technique of determining the variance permitted by the term "about." In other cases, the gradations in a series of values may be used to determine the range of variance permitted by the term "about." Further, all ranges in the present disclosure are inclusive and combinable, and references to values stated in ranges include every value within that range.

As discussed above, energy storage systems that are operable on a large scale while maintaining high efficiency values can be extremely desirable. Flow batteries employing coordination complexes as active materials have generated significant interest in this regard. Exemplary description of illustrative flow batteries, their use, and operating characteristics is provided hereinbelow. Titanium coordination complexes, particularly those containing at least one catecholate ligand, can be especially desirable due to their favorable half-cell potentials and high current efficiency values, among other factors. Although various techniques are presently available in the art for synthesizing titanium catechol complexes, none are believed to be suitable for producing high-purity active materials at the very large (multi-pound up to multi-ton) scales needed to support commercial energy storage applications. Raw material costs, labor expenses, low yields and insufficient purity are among the factors that can be problematic at present for supplying commercially viable quantities of these types of active materials. Other metal complexes containing alternative metal centers and/or ligands differing from catecholate ligands can be similarly problematic in this regard.

As used herein, the term "catechol" refers to a compound having an aromatic ring bearing hydroxyl groups on adjacent carbon atoms (i.e., 1,2-hydroxyl groups). Optional substitution can also be present in addition to the 1,2-hydroxyl groups. As used herein, the term "catecholate" refers to a substituted or unsubstituted catechol compound that is bound to a metal center via a metal-ligand bond, particularly a titanium metal center. As used herein, the term "unsubstituted catecholate" refers to the particular case where 1,2-dihydroxybenzene (catechol) is bound to a metal center via a metal-ligand bond. The optional substitution on catecholate ligands can serve a number of purposes such as, for example, altering the solubility characteristics and/or half-cell potentials of the metal complexes that they produce. Monosulfonated catecholate ligands, for example, can improve the solubility of titanium coordination complexes while maintaining desirable electrochemical properties that are at least comparable to those obtained when only unsubstituted catecholate ligands are present. As used herein, the term "monosulfonated" refers to one sulfonic acid group or any salt thereof being present on an aromatic ring. Catecholate ligands bearing an additional hydroxyl group, such as pyrogallol, 1,2,4-trihydroxybenzene and gallic acid, for example, can be similarly advantageous in this regard. Catecholates such as the foregoing can also be optionally further substituted. Other advantageous catecholate ligands bearing further substitution are discussed hereinbelow. It is to be understood that catechols and catecholates suitable for use in the present disclosure also include positional isomers that are not necessarily specifically illustrated herein. In addition, monosubstituted catechols and catecholates can also be polysubstituted in some embodiments, particularly disubstituted or trisubstituted, unless otherwise indicated herein.

The present inventors discovered processes for synthesizing titanium catechol complexes that can proceed from readily available and relatively inexpensive starting materials. Namely, the syntheses described herein take place using common organic solvents and employ readily available titanium reagents such as titanium tetrachloride and other titanium tetrahalides, titanium oxyhalides, titanium oxysulfate, and titanium alkoxides. These titanium reagents produce byproduct species that can be removed through various means in the course of forming an aqueous electrolyte solution containing the titanium catechol complexes in a suitable salt form, such as an alkali metal salt form. Syntheses of the complexes can be conducted on a wide range of scales, ranging from gram-scale laboratory processes up to multi-ton production. Because the syntheses described herein produce one or more removable byproduct species, the titanium catechol complexes can be obtained with good purity levels in high-concentration aqueous phases that can be suitable for use in flow batteries and other electrochemical energy storage systems with little to no further processing. In particular, the syntheses described herein allow the titanium catechol complexes to be produced in the aqueous phase without forming significant amounts of extraneous salts, such as extraneous alkali metal halide salts, that are not associated with the titanium catechol complexes in their desired salt form. The syntheses described herein can limit the formation of extraneous salts through judicious removal of the byproduct species produced when initially forming the titanium catechol complexes. If not removed, the byproduct species, in some cases, can react to produce the extraneous salts and can complicate the stoichiometry of base addition.

More specifically, the syntheses described herein allow an intermediate titanium catechol complex to be initially formed through reacting a titanium reagent with a catechol compound in an organic solvent. In many organic solvents, the intermediate titanium catechol complex precipitates from the reaction mixture, which helps drive the reaction toward complete conversion of the starting materials. Since the reaction stops at an insoluble intermediate stage, byproduct species can be removed from the reaction mixture at this point before converting the intermediate titanium catechol complex into a desired salt form in an aqueous phase. For example, HCl and other hydrogen halide gases, which can form as a byproduct of the reaction when halide-containing titanium reagents are used, can be driven off to substantial completion before forming an aqueous phase containing the salt form titanium catechol complex in an at least partially dissolved form. Byproduct species, such as HCl and other hydrogen halides, if they remain present, can react with the bases used in conjunction with converting the titanium catechol complex into its salt form and produce extraneous salts. The extraneous salts produced upon reaction of the base with the byproduct species can be detrimental in many instances. For example, extraneous salts can decrease solubility of the salt form titanium catechol complexes through a common ion effect. In addition, the reaction of the byproduct species with the base can prevent the intermediate titanium catechol complex from being completely converted into its desired salt form. Byproduct species other than hydrogen halides can also result in similar issues as well as additional challenges, and their removal at the intermediate titanium catechol complex stage can also be desirable. In some instances, the byproduct species can be removed from the intermediate titanium catechol complex without isolating the intermediate titanium catechol complex. In other cases, however, removal of the byproduct species can be conducted in a more facile manner by isolating the intermediate titanium catechol complex, thereby removing the byproduct species, and then forming the salt form titanium catechol complex.

In some embodiments, the intermediate titanium catechol complex can be converted into an alkali metal salt form titanium catechol complex through reaction with an alkaline aqueous solution containing an alkali metal base. As used herein, the term "alkali metal" refers to a metal in Group I of the periodic table, such as lithium, sodium or potassium. Sodium, potassium, or mixed sodium/potassium salt forms can be particularly desirable salt forms for incorporation in an electrolyte solution. Although an alkali metal salt form titanium catechol complex can be advantageous for use in conjunction with the components of flow batteries and other electrochemical systems, it is to be recognized that alternative salt forms can be synthesized using other bases. For example, alkaline earth metal salt form titanium catechol complexes can be synthesized by using an alkaline earth metal base, such as calcium hydroxide. Other salt forms, such as ammonium, phosphonium, sulfonium, tetraalkylammonium, tetraarylammonium, mixed alkyl and aryl tetrasubstituted ammonium, tetraarylphosphonium, iminium, and nitronium salt forms, can also be prepared and used similarly. Mixed salt forms, which can desirably have improved aqueous phase solubility in some cases, are also possible in some embodiments of the present disclosure.

Unlike the intermediate titanium catechol complexes, alkali metal salt form titanium catechol complexes and other salt forms of these complexes are readily soluble in the aqueous phase resulting from addition of the alkaline aqueous solution to the intermediate titanium catechol complex. By carefully controlling the stoichiometric quantity of base that is added to the intermediate titanium catechol complex (based upon the molar amount of the titanium reagent that is initially present), a desired pH can be obtained in the aqueous phase resulting from conversion of the intermediate titanium catechol complex into its desired salt form. Moreover, because the syntheses described herein allow substantial removal of byproduct species to take place from the reaction mixture before adding the alkaline aqueous solution thereto, particularly byproduct species that can form extraneous salts upon the addition of base, essentially all of the base can go toward converting the intermediate titanium catechol complex into the corresponding salt form rather than forming an extraneous salt not associated with the salt form titanium catechol complex in the aqueous phase, particularly alkali metal halide salts or other alkali metal salt in the case of an alkali metal base. Avoiding the formation of alkali metal halide salts and other extraneous salts in the aqueous phase can be desirable in order to maintain high solubility levels for the salt form titanium catechol complexes, which might otherwise be decreased due to a common ion effect in the presence of extraneous metal salts. In some embodiments of the present disclosure, alkali metal halide salts or other extraneous salts can be present at levels of about 0.01 equivalents or less relative to the salt form titanium catechol complex in the aqueous phases produced by the methods described herein.

As a further advantage, by utilizing an organic solvent that is immiscible with water, the resulting aqueous phase containing the salt form titanium catechol complex can be readily isolated by various phase partitioning techniques. Because minimal workup is needed when an immiscible solvent is used, production runs can provide large quantities of aqueous phase product in a relatively short amount of time. Accordingly, the syntheses described herein are readily amenable to scale up to a desired level. Further, the syntheses described herein can be readily extended to continuous syntheses, rather than batchwise processes. Although organic solvents that are immiscible with water can be advantageous for the reasons noted above, water-miscible organic solvents can also be suitable and advantageous in some instances, as described further herein. In some instances, for example, an alcohol byproduct produced when utilizing a titanium alkoxide as the titanium reagent can become incorporated in the organic solvent and/or in the aqueous phase containing the salt form titanium catechol complex.

Although titanium catechol complexes can be advantageous in the syntheses and further applications described herein, other metal catechol complexes can also be suitable in this regard. Metal catechol complexes containing alternative metals such as, for example, Al, Ca, Co, Cr, Sr, Cu, Fe, Hf, Mg, Mn, Mo, Ni, Pd, Pt, Ru, Sn, Zn, Zr, V, W and U can be synthesized through similar procedures and utilized as the active material for a flow battery. Lanthanides and actinides can also be suitable in this regard. Like titanium, Zr and Hf coordination compounds can possess highly desirable properties for incorporation as an active material in a flow battery. Accordingly, the disclosure herein directed to titanium can be extended to the foregoing alternative metals without limitation by one having ordinary skill in the art.

Furthermore, the disclosure herein can be extended to titanium and other metal coordination complexes that contain only catecholate ligands, combinations of one or more catecholate ligands with other non-catecholate ligands, or only non-catecholate ligands. Suitable non-catecholate ligands can include any of monodentate, bidentate or tridentate ligands, and some examples of suitable non-catecholate ligands are provided below.

In various embodiments, the present disclosure describes methods including: forming a catechol solution containing a catechol compound and an organic solvent; contacting a titanium reagent with the catechol solution to form a reaction mixture; reacting the titanium reagent with the catechol compound to form an intermediate titanium catechol complex and a byproduct species; separating the byproduct species from the intermediate titanium catechol complex; and combining an alkaline aqueous solution containing a base with the intermediate titanium catechol complex. The base converts the intermediate titanium catechol complex into a salt form titanium catechol complex that is at least partially dissolved in an aqueous phase.

In further embodiments, the methods can include separating the aqueous phase and an organic phase from one another. The aqueous phase can be substantially free of byproducts formed before or during the production of the salt form titanium catechol complex, such as metal halides or other extraneous salts, as discussed herein. For example, the aqueous phase can be substantially free of extraneous salts formed from a reaction between anions introduced from the titanium reagent and cations introduced from the base used to generate the salt form titanium catechol complexes. The reactive byproduct species introduced from the titanium reagent can be removed without otherwise isolating the intermediate titanium catechol complex, or the intermediate titanium catechol complex can be isolated in some cases to affect removal of the byproduct species. Suitable techniques for separating the aqueous phase can include various solvent partitioning techniques, which can be predicated upon the use of an organic solvent that is substantially water-immiscible. In embodiments in which the intermediate titanium catechol complex undergoes isolation, the aqueous phase can be formed directly without undergoing separation from an organic phase used to form the intermediate titanium catechol complex.

Catechol compounds suitable for use in the various embodiments described herein are not considered to be particularly limited. In some embodiments, the catechol compound can be o-catechol itself (i.e., unsubstituted 1,2-dihydroxybenzene). In some or other embodiments, the catechol compound can include at least one substituted catechol compound, which can optionally be present in combination with an unsubstituted catechol compound. Accordingly, the intermediate titanium catechol complexes and salt form titanium catechol complexes described herein can include unsubstituted catecholate ligands, substituted catecholate ligands, or any combination thereof. In further embodiments, additional ligands that are non-catecholate in nature can also be present in combination with substituted or unsubstituted catecholate ligands. As mentioned above, non-catecholate ligands and other metals can also be used in alternative embodiments of the present disclosure. In particular embodiments, 3,4-dihydroxybenzenesulfonic acid can be an especially desirable substituted catechol compound for use in forming a salt form titanium catechol complex. Pyrogallol, 1,2,4-trihydroxybenzene and gallic acid are also substituted catechol compounds that can be particularly desirable. These and other similar catechol compounds can be further substituted in some embodiments.

Other examples of substituted catechol compounds that can be suitable for use in the embodiments described herein can include those bearing solubilizing groups to increase the aqueous solubility of the resulting complexes. Non-limiting examples of substituted catechol compounds that can be suitable for use in the embodiments described herein can include those having a structure of

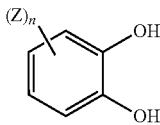

in a neutral form or a salt form. Z is a heteroatom functional group selected from the group consisting of $A^1R^{41}$, $A^2R^{42}$, $A^3R^{43}$, CHO, and sulfonic acid. Variable n is an integer ranging between 1 and 4, such that one or more Z are bound to the substituted catechol compound at an open aromatic ring position. Each Z is the same or different when more than one Z is present. $A^1$ is $-(CH_2)_a-$ or $-(CHOR)(CH_2)_a-$, $R^{41}$ is $-OR^1$ or $-(OCH_2CH_2O)_bR^1$, a is an integer ranging between 0 and about 6, and b is an integer ranging between 1 and about 10. $A^2$ is $-(CH_2)_c-$ or $-CH(OR^2)(CH_2)_d-$, $R^{42}$ is $-NR^3R^4$, a carbon-linked amino acid, or $-C(=O)XR^5$, X is $-O-$ or $-NR^6-$, c is an integer ranging between 0 and about 6, and d is an integer ranging between 0 and about 4. $A^3$ is $-O-$ or $-NR^2-$, $R^{43}$ is $-(CHR^7)_e OR^1$, $-(CHR^7)_e NR^3R^4$, $-(CHR^7)_e C(=O)XR^5$, or $-C(=O)(CHR^7)_f R^8$, e is an integer ranging between 1 and about 6, and f is an integer ranging between 0 and about 6. R is H, $C_1$-$C_6$ alkyl, heteroatom-substituted $C_1$-$C_6$ alkyl, or $C_1$-$C_6$ carboxyalkyl. $R^1$ is H, methyl, ethyl, a $C_2$-$C_6$ polyol bound through an ether linkage or an ester linkage, or $C_1$-$C_6$ carboxyalkyl. $R^2$, $R^3$, $R^4$ and $R^6$ are independently selected from the group consisting of H, $C_1$-$C_6$ alkyl, or heteroatom-substituted $C_1$-$C_6$ alkyl. $R^5$ is H, $C_1$-$C_6$ alkyl, heteroatom-substituted $C_1$-$C_6$ alkyl, a $C_2$-$C_6$ polyol bound through an ester linkage, a hydroxyacid bound through an ester linkage, a polyglycol acid bound through an ester linkage, an amino alcohol bound through an ester linkage or an amide linkage, an amino acid bound through an ester linkage or an amide linkage, or $-(CH_2CH_2O)_bR^1$. $R^7$ is H or OH. $R^8$ is H, $C_1$-$C_6$ alkyl, heteroatom-substituted $C_1$-$C_6$ alkyl, a $C_2$-$C_6$ polyol bound through an ether linkage or an ester linkage, a hydroxyacid bound through an ether linkage or an ester linkage, a polyglycol acid bound through an ether linkage or an ester linkage, an amino alcohol bound through an ether linkage, an ester linkage, or an amide linkage, an amino acid bound through an ether linkage, an ester linkage, or an amide linkage, a carbon-linked amino acid, or $-(OCH_2CH_2O)_bR^1$. In some embodiments, substituted catechol compounds of the structure shown above can be covalently bonded to another such structure, each of which can be independently substituted with $(Z)_n$ as set forth above. Such structures can be joined to one another a single bridging group or a double bridging group.

Without being bound by any theory or mechanism, it is believed that the intermediate titanium catechol complex produced in the embodiments of the present disclosure has a formula of $$H_2Ti(L)_3,$$

wherein L represents an unsubstituted or substituted catecholate ligand, a bidentate non-catecholate ligand or any combination thereof, where at least one L is a substituted or unsubstituted catecholate ligand. That is, the intermediate titanium catechol complex is believed to be a "protonated" ion pair of a titanium-based complex anion. Further, when monodentate non-catecholate ligands are present, additional equivalents of L (i.e., >3) can be present to produce a coordination number of 6 on the titanium center, the most common coordination number for Ti (IV).

As indicated above, the intermediate titanium catechol complex can be converted into a salt form titanium catechol complex through reaction with a base, such as an alkali metal base. Again remaining unbound by any theory or mechanism, it is believed that such salt form titanium catechol complexes can have a formula of $$D_{1-6}Ti(L)_3,$$

wherein D is metal cation, ammonium cation, tetraalkylammonium cation, or phosphonium cation and L is defined as above. The molar equivalents of D can range between 1 and 6 depending on whether D is a monovalent or divalent cation, and whether L contains any ionizable functional groups. For example, when D is a monovalent cation, such as an alkali metal ion, and L represents an uncharged catecholate ligand, 2 molar equivalents of the alkali metal ion are present to maintain charge balance (i.e., the salt form titanium catechol complexes have a formula of $D_2Ti(L)_3$). When the alkaline aqueous solution contains a base that is not an alkali metal base, such as an alkaline earth metal base, D can also include any alternative cations (e.g., a single alkaline earth metal ion, a mixture of alkaline earth metal ions, phosphonium and/or ammonium ions), optionally in combination with one or more alkali metal ions, in which case the molar equivalents of D reflect the amount needed to maintain charge balance. In some embodiments, a single type of substituted or unsubstituted catecholate ligand can be present in the complexes. In other embodiments, mixtures of two or more unsubstituted and/or substituted catecholate ligands can be present. In still other embodiments, ligands that are non-catecholate ligands can be present. For example, in some embodiments, the salt form titanium catechol complexes can have a formula of $$D_{1-6}Ti(L_1)(L_2)(L_3),$$

wherein D is defined as above and $L_1$-$L_3$ are ligands, provided that at least one of $L_1$-$L_3$ is a catecholate ligand or a substituted catecholate ligand. In some specific embodiments, two catecholate ligands can be present, and in other specific embodiments, three catecholate ligands can be present. Alternative ligands that can constitute the balance of $L_1$-$L_3$ include, but are not limited to, certain exemplary ligands described hereinbelow. When at least one monodentate non-catecholate ligand is present, additional ligands beyond just three ligands (i.e., $L_1$, $L_2$ and $L_3$) can be present to an amount necessary to achieve a full coordination sphere.

In more specific embodiments, salt form titanium catechol complexes of the present disclosure can have a formula of $$Na_mK_nLi_oTi(L)_3,$$

wherein m+n+o=2, provided that L does not bear a charged functional group, and L is defined as above. For example, in the case of at least one catecholate ligand (L) bearing a negatively charged functional group, such as a sulfonic acid anion, greater than two molar equivalents of sodium and/or potassium ions are needed to maintain charge balance. In more particular embodiments, o=0 and m+n=2, such that the salt form is a sodium and/or potassium salt form. In still more particular embodiments, both m and n are non-zero numbers, and they can be equal or non-equal to one another. In some embodiments, a ratio of m to n can range between about 1:10 to about 10:1, or between about 1:5 or about 5:1. In some embodiments, substantially equal molar quantities of sodium and potassium can be present in the salt form titanium catechol complexes. As indicated above, non-catecholate ligands can also be present in such complexes.

Accordingly, in more general embodiments, the salt form titanium catechol complexes disclosed herein can have a formula of

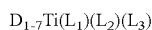

$D_{1\text{-}7}Ti(L_1)(L_2)(L_3)$ where, in this case, D is a monovalent or divalent cation (e.g., an alkali metal cation, an alkaline earth metal cation, an ammonium cation, a tetraalkylammonium cation, a phosphonium cation, or other alternative cation), and $L_1$-$L_3$ are bidentate ligands, provided that at least one of $L_1$-$L_3$ is a catecholate ligand or a substituted catecholate ligand, and one or more of $L_1$-$L_3$ optionally bears a positive or negative charge. The molar equivalents of D that are present depend both upon the charge of D and the charge, if any, borne by $L_1$-$L_3$. In more particular embodiments, the salt form titanium catecholate complexes can have a formula of

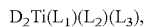

$D_2Ti(L_1)(L_2)(L_3)$, where, in this case, D is a monovalent cation or a mixture of monovalent cations, and $L_1$-$L_3$ are defined as above.

The salt form of the titanium catechol complexes can depend upon the cation associated with the base used to promote formation of the salt form. Suitable bases are not considered to be particularly limited, provided that they have sufficient basicity to produce the salt form titanium catechol complex. Suitable bases can include, for example, a metal hydroxide, a metal oxide, a metal bicarbonate, a metal carbonate, an ammonium base, a tetraalkylammonium base, a deprotonated ligand base, an amine, a borate, a metal borohydride, a metal hydride, a metal phosphate, a sulfonium base, a phosphazenium base, a guanidinium base, a metal azide, a cyanate base, a thiocyanate base, a metal carboxylate, a phenolate base, a carbamate base, an imide base, a deprotonated sulfonamide base, a nitroxyl base, a basic anion-exchange resin, a metal chalcogenide, a phosphonium base, a tetraalkylphosphonium base, a tetraarylphosphonium base, or any combination thereof. Although some of these bases produce salt form titanium catechol complexes that are more soluble in an aqueous phase, others may be more beneficial for forming an organic phase containing the titanium catechol complexes in their salt form.

In some embodiments of the present disclosure, the base can be an alkali metal base or combination of alkali metal bases. In some embodiments, the alkali metal base can include an alkali metal hydroxide such as sodium hydroxide, potassium hydroxide, or any combination thereof. In more particular embodiments, the alkali metal base can be a mixture of sodium hydroxide and potassium hydroxide. The molar ratios of the sodium hydroxide and potassium hydroxide can lie within the ranges disclosed above. Complexes having mixed sodium and potassium counterions can be especially desirable due to their potentially increased solubility values compared to those obtained when only a single alkali metal counterion is present.

In alternative embodiments of the present disclosure, alkali metal bases such as alkali metal oxides, alkali metal carbonates, and alkali metal bicarbonates can be used to convert the intermediate titanium catechol complex into the salt form titanium catechol complex. Optionally, these alkali metal bases can be used in combination with the alkali metal hydroxide bases discussed above. Again, a mixture of sodium and potassium counterions can be introduced through the choice of the alkali metal bases present in the alkaline aqueous solution. For example, an alkali metal hydroxide having a first alkali metal counterion can be combined with an alkali metal carbonate or bicarbonate having a second alkali metal counterion to accomplish the foregoing.

As still another alternative to alkali metal bases, ammonium bases, such as ammonium hydroxide, can also be used in some embodiments of the present disclosure. In some embodiments, the alkaline aqueous solution can contain a mixture of ammonium hydroxide and an alkali metal base, in which case the resulting salt form titanium catechol complex can contain a mixture of ammonium and alkali metal counterions. Some ammonium cations can be alkyl substituted, such as tetraalkylammonium cations, and can be suitably incorporated in the salt form titanium catechol complexes.

In some embodiments, ligands in addition to substituted or unsubstituted catecholate ligands can be present in the complexes described herein. Other ligands that can be present alternatively and/or in combination with catecholate ligands include, for example, amines, diamines, amino alcohols, amino acids, ascorbate, citrate, glycolate, a polyol, gluconate, hydroxyalkanoate, acetate, formate, benzoate, malate, maleate, phthalate, sarcosinate, salicylate, oxalate, urea, polyamine, aminophenolate, acetylacetonate, and lactate. Where chemically feasible, it is to be recognized that such ligands can be optionally substituted with at least one group selected from among $C_{1\text{-}6}$ alkoxy, $C_{1\text{-}6}$ alkyl, $C_{1\text{-}6}$ alkenyl, $C_{1\text{-}6}$ alkynyl, 5- or 6-membered aryl or heteroaryl groups, a boronic acid or a derivative thereof, a carboxylic acid or a derivative thereof, cyano, halide, hydroxyl, nitro, sulfonate, a sulfonic acid or a derivative thereof, a phosphonate, a phosphonic acid or a derivative thereof, or a glycol, such as polyethylene glycol. Compositions such as glycols having a hydrocarbon backbone can optionally contain one or more double or triple carbon-carbon bonds. Alkanoate includes any of the alpha, beta, and gamma forms of these ligands. Polyamines include, but are not limited to, ethylenediamine, ethylenediamine tetraacetic acid (EDTA), and diethylenetriamine pentaacetic acid (DTPA).

Other examples of ligands that can be present in the complexes of the present disclosure can include monodentate, bidentate, and/or tridentate ligands. Examples of monodentate ligands that can be present in the complexes of the present disclosure include, for example, carbonyl or carbon monoxide, nitride, oxo, hydroxo, water, sulfide, thiols, pyridine, pyrazine, and the like. Examples of bidentate ligands that can be present in the complexes of the present disclosure include, for example, bipyridine, bipyrazine, ethylenediamine, diols (including ethylene glycol), and the like, any of which can contain optional carbon-carbon double or triple bonds. Examples of tridentate ligands that can be present in the complexes of the present disclosure include, for example, terpyridine, diethylenetriamine, triazacyclononane, tris(hydroxymethyl)aminomethane, and the like.

In some embodiments, the titanium reagent can be added neat to the catechol solution in the organic solvent. Neat addition can be particularly desirable for liquid titanium reagents such as titanium tetrachloride and titanium isopropoxide. In other embodiments, a solution of the titanium reagent in an organic solvent can be added to the catechol solution. Addition of the titanium reagent in a solution can be particularly desirable for facilitating the addition of solid titanium reagents. Depending upon the scale at which the reaction is run, adding a solution of liquid titanium reagents, such as titanium tetrachloride, can also be desirable for facilitating transfer of these reagents compared to neat transfer. For example, at smaller reaction scales, where the amount of added titanium tetrachloride is smaller, transferring a solution of titanium tetrachloride can be easier to accomplish.

Suitable organic solvents for utilization in the various embodiments described herein are not considered to be particularly limited. In some embodiments, the organic solvent can be non-reactive toward the titanium reagent and substantially water-immiscible. Non-limiting examples of suitable organic solvents include aprotic organic solvents that are water-immiscible such as toluene, xylenes, benzene, ligroin, hexane, cyclohexane, dichloromethane, dichloromethane, ethyl ether, isopropyl ether, methyl t-butyl ether, and any combination thereof. Water-immiscible organic solvents of this type can be particularly desirable for their utility in processing the intermediate titanium catechol complex into the salt form titanium catechol complex, as discussed further herein. In addition, such water-immiscible organic solvents do not have significant affinity for retaining hydrogen halide gases formed during the reaction between the catechol compound and certain titanium reagents of the present disclosure, thereby allowing this gaseous reaction byproduct species to be substantially driven off from the reaction mixture prior to combining the alkaline aqueous solution to transform the intermediate titanium catechol complex into the salt form titanium catechol complex.

In some embodiments, organic solvents that have some measure of water miscibility can also be suitable. In this regard, suitable organic solvents can include, for example, tetrahydrofuran (THF), acetonitrile, dioxane, dimethylformamide, dimethylsulfoxide, and any combination thereof. Water-miscible organic solvents can be used alone in some embodiments, or they can be used in combination with a water-immiscible organic solvent in other embodiments. In the case where a water-miscible organic solvent is used, the aqueous phase resulting from formation of the salt form titanium catechol complex can retain at least a portion of the organic solvent therein. Residual organic solvent in the aqueous phase can improve solubility of the salt form titanium catechol complex in some instances. If the presence of organic solvent in the aqueous phase is undesired, however, the residual solvent can be removed from the aqueous phase by various distillation, washing or solvent exchange processes. These processes can also be used to remove trace quantities of admixed water-immiscible organic solvents, if needed or desired.

In still other embodiments, alcohol solvents can be suitable for use in the syntheses described herein. Although alcohol solvents are reactive with titanium tetrachloride and some other titanium reagents to produce titanium alkoxides and HCl gas or other hydrogen halides as byproduct species, the titanium alkoxides can react further to form an intermediate titanium catechol complex. Upon forming the intermediate titanium catechol complex, the alcohol is regenerated. The HCl gas or other hydrogen halide byproduct species can be removed from the reaction mixture in accordance with the disclosure herein. The alcohol solvent can either be left in the reaction mixture, where it can function as co-solvent after forming the salt form titanium catechol complex, or it can be removed from the reaction mixture by the various processes described above. In some embodiments, alcohol solvents can be used in combination with any of the other organic solvents mentioned above.

In some embodiments, suitable titanium reagents can include titanium tetrahalides and titanium oxyhalides. Suitable titanium tetrahalides can include titanium tetrachloride, titanium tetrabromide, titanium tetraiodide, and titanium mixed tetrahalides. As used herein, the term "titanium mixed tetrahalide" refers to a titanium tetrahalide containing two or more different halides, such as $TiCl_3Br$, $TiCl_2Br_2$ and $TiClBr_3$. These titanium reagents are all molecular compounds and can readily react according to the embodiments described herein. Titanium tetrafluoride and the related $TiF_6^{2-}$ complex anion are extended polymeric solids and can react with ligatable compounds less readily. In addition, titanium tetrafluoride and $TiF_6^{2-}$ generate hydrogen fluoride, which can be especially problematic to address from a manufacturing standpoint due to its high reactivity and toxicity.

Suitable titanium oxyhalide reagents can include titanium oxychloride ($TiOCl_2$), titanium oxybromide ($TiOBr_2$) and titanium oxyiodide ($TiOI_2$). The related titanium oxyfluoride compound can present similar handling and toxicity issues as titanium tetrafluoride, although it can be used suitably in some instances.

Titanium tetrahalides, titanium mixed tetrahalides, and titanium oxyhalides react to release a hydrogen halide gas as a byproduct species upon contacting a ligatable compound, such as a catechol compound. As indicated above, suitable organic solvents for conducting the syntheses described herein can lack significant affinity for retaining HCl gas or other hydrogen halide gases, thereby allowing the HCl gas or other hydrogen halide gas to be substantially removed from the reaction mixture before combining the alkaline aqueous solution with the intermediate titanium catechol complex. Removal of the HCl gas or other hydrogen halide gas allows the salt form titanium catechol complex to be formed in an aqueous phase without generating an appreciable amount of extraneous salts through reaction of the HCl gas with the base. As discussed above, avoiding the production of extraneous salts, such as alkali metal halide salts, can be desirable for improving solubility of the salt form titanium catechol complexes. Additional measures can also be taken to ensure that residual quantities of HCl gas or other hydrogen halide gases are removed from the reaction mixture before adding the alkaline aqueous solution thereto and forming the salt form titanium catechol complex. Reduced pressure, inert gas purge, heat or any combination thereof can be employed to remove residual HCl gas or other hydrogen halide gases, as discussed hereinafter.

In some embodiments, the reaction mixture can be maintained at a reduced pressure before adding the alkaline aqueous solution thereto. As used herein, the term "reduced pressure" refers to any pressure below normal atmospheric pressure, which is 760 torr at sea level. In some embodiments, suitable reduced pressures for removing HCl gas or other hydrogen halide gases from the reaction mixture can range between about 50 torr and about 400 torr, or between about 100 torr and about 200 torr. The normal boiling point of the organic solvent can dictate to some extent how much the pressure can be reduced to affect removal of HCl gas or another hydrogen halide gas from the reaction mixture. In general, the pressure should be maintained such that loss of the organic solvent is minimal. For example, in the case of lower boiling solvents such as dichloromethane, higher pressures may be needed to preclude solvent loss compared to those that can be utilized when employing higher boiling solvents, such as xylenes.

In some embodiments, a flowing inert gas can contact the reaction mixture while evolving the HCl gas or other hydrogen halide gas therefrom. Suitable inert gases can include, for example, nitrogen, helium, argon, neon, or the like. Similar to the reduced pressure operations discussed above, the flowing inert gas can promote removal of HCl gas or other hydrogen halide gases from the reaction mixture.

As discussed above, the intermediate titanium catechol complex can also be isolated from the reaction mixture prior to formation of the salt form titanium catechol complex to facilitate separation from a hydrogen halide byproduct species. Since the intermediate titanium catechol complex is often insoluble in the reaction mixture, suitable processes for isolating the intermediate titanium catechol complex can include, for example, filtration, centrifugation, decantation, and the like, accompanied by optional washing with a solvent in which the intermediate titanium catechol complex is insoluble.

In most instances, the intermediate titanium catechol complex is insoluble in the reaction mixture in the syntheses described herein. As indicated above, precipitation of the intermediate titanium catechol complex can help drive the reaction to completion, as well as provide a visual indicator of when the reaction is complete. For most aprotic organic solvents that are substantially water-immiscible, the intermediate titanium catechol complex is insoluble, which can make these organic solvents especially desirable for use in the embodiments of the present disclosure. The intermediate titanium catechol complex is also insoluble in some water-miscible solvents, and such solvents can also be desirable for use in some embodiments described herein, such as instances wherein some residual organic solvent in the aqueous phase can be tolerated.

In principle, the intermediate titanium catechol complex can be isolated from the reaction mixture and undergo optional purification before being combined with the alkaline aqueous solution. Isolation and/or purification can be particularly facile in instances where the intermediate titanium catechol complex is insoluble in the organic solvent. Isolation and/or purification of the intermediate titanium catechol complex can provide another measure for removal of residual HCl gas or other hydrogen halides that would otherwise form extraneous salts upon converting the intermediate titanium catechol complex into the salt form titanium catechol complex. Isolation and purification of the intermediate titanium catechol complex can also be performed if residual quantities of the organic solvent are undesirable when forming the aqueous phase containing the salt form titanium catechol complex or if removal of residual quantities of organic solvent would be problematic or expensive. Additional impurities, such as reaction byproduct species and unreacted starting materials, can also be removed through isolation of the intermediate titanium catechol complex before its conversion into the corresponding salt form.

More desirably, however, the intermediate titanium catechol complex can be reacted in situ without isolation from the reaction mixture before combining the alkaline aqueous solution. In situ reaction of the intermediate titanium catechol complex can be less labor intensive and less costly compared to instances where additional isolation and purification operations are performed. In more specific embodiments, the intermediate titanium catechol complex and the salt form titanium catechol complex can be formed consecutively in a single reaction vessel.

Other titanium reagents can also be used in some embodiments of the present disclosure. For example, in some embodiments titanocene dichloride [i.e., bis(cyclopentadienyl)titanium (IV) dichloride] can be used as the titanium reagent. This titanium reagent reacts with ligatable compounds to displace the chloride ligands to produce titanium complexes in which the cyclopentadienyl ligands are still coordinated to the titanium center. That is, in the case of the reaction between titanocene dichloride with a catechol compound, titanium catechol complexes having the formula $Cp_2Ti(cat)$ are produced, where Cp is a cyclopentadienyl ligand and cat is substituted or unsubstituted catecholate ligand. Since these titanium catechol complexes are uncharged unless the cyclopentadienyl or catecholate ligands bear an ionizable functional group, these complexes are not convertible into a salt form. Of course, if the catecholate ligand is substituted and bears an ionizable functional group, an appropriate salt form can be produced.

In some embodiments, titanium hydrides can be a suitable titanium reagent in the syntheses described herein.

As mentioned above, titanium alkoxides can be generated in situ through reacting a titanium tetrahalide or titanium oxyhalide with an alcohol solvent. The hydrogen halides generated during this process can be similarly addressed in a similar manner to that described above. In other embodiments, previously produced titanium alkoxides can be utilized in the embodiments of the present disclosure. Use of previously produced titanium alkoxides is addressed further hereinbelow.

Titanium reagents other than those that generate hydrogen halide gases upon reaction with a ligatable compound can also be used in conjunction with the present disclosure. These alternative byproduct species can be removed from the reaction mixture in the same manner or in a different manner than how hydrogen halide gases are removed.

Titanium oxysulfate, for instance, can be a suitable titanium reagent in some embodiments. Titanium oxysulfate forms sulfuric acid as a byproduct species when contacted with a ligatable compound, such as a catechol compound. Due to its relatively low volatility, separation of the sulfuric acid from the intermediate titanium catechol complex by converting the sulfuric acid to the gas phase can be difficult. In the case of a sulfuric acid byproduct species, isolation of the intermediate titanium catechol complex from the reaction mixture can be desirable. The isolation of the intermediate titanium catechol complex from the reaction mixture can be complete, such as by completely removing the mother liquor (supernatant liquid) from the intermediate titanium catechol complex. In the case of complete isolation of the intermediate titanium catechol complex, the sulfuric acid can remain with the mother liquor and not contribute to the formation of extraneous sulfate salts once the intermediate titanium catechol complex is converted into its salt form in an aqueous phase. In some instances, the organic solvent can be chosen such that the sulfuric acid is immiscible, thereby allowing separation of the sulfuric acid to take place by decantation or other phase separation technique. In still other instances, the sulfuric acid can be contacted with an organic solvent which is immiscible with the organic solvent used for forming the intermediate titanium catechol complex and in which the sulfuric acid itself is miscible, thereby allowing separation of the sulfuric acid byproduct species to take place by a phase separation technique.

In still another alternative, the sulfuric acid can be converted into a highly insoluble sulfate salt that is insoluble upon forming the aqueous phase containing the salt form titanium catechol complex. Suitable insoluble sulfates can include, for example, alkaline earth metal sulfates such as calcium sulfate or barium sulfate. For example, a sufficient amount of alkaline earth base, such as calcium hydroxide, can be contacted with the reaction mixture to convert the sulfuric acid into an alkaline earth sulfate salt. The amount of alkaline earth base can be chosen based on the stoichiometric amount of sulfuric acid that should be formed from the titanium oxysulfate reagent, thereby avoiding the introduction of extraneous alkaline earth metal ions into the aqueous phase once it is formed and potentially leading to a different extraneous salt. Upon forming the aqueous phase, a desired salt form titanium catechol complex, such as an alkali metal salt form, can be generated without producing extraneous sulfate salts dissolved or precipitated in the aqueous phase. An amount of the base used to generate the desired salt form titanium catechol complex can be chosen based upon the stoichiometric amount of the intermediate titanium catechol complex that should be present, again to preclude the formation of extraneous salts in the aqueous phase. Alternately, the reaction mixture can be treated with an aqueous solution containing a sufficient amount of the alkaline earth base to convert the sulfuric acid into an alkaline earth sulfate and to produce the alkaline earth metal salt form of the titanium catechol complex. In either case, the precipitated alkaline earth metal sulfate can be separated (e.g., via filtration) from the salt form titanium catechol complex in the aqueous phase.

Titanium alkoxides generate an alcohol upon forming the intermediate titanium catechol complex. As discussed above, hydrogen halides can also be generated when forming titanium alkoxides in situ in the presence of an alcohol solvent. Since an alcohol byproduct does not lead to the formation of extraneous salts upon generation of the salt form titanium catechol complex unless very strong bases (e.g., metal hydrides) are used, it is usually possible to leave this byproduct in the reaction mixture and potentially in the ensuing aqueous phase containing the salt form titanium catechol complex. Accordingly, in some embodiments, methods of the present disclosure can include: forming a catechol solution containing a catechol compound and an organic solvent; combining a titanium alkoxide with the catechol solution to form a reaction mixture; reacting the titanium alkoxide with the catechol compound to form an intermediate titanium catechol complex and an alcohol; and without separating the intermediate titanium catechol complex from the alcohol, combining an alkaline aqueous solution containing a base with the intermediate titanium catechol complex. The base converts the intermediate titanium catechol complex into a salt form titanium catechol complex that is at least partially dissolved in an aqueous phase further containing the alcohol. Alcohol solvents can similarly become incorporated in the aqueous phase when titanium alkoxides are generated in situ.

In some embodiments, the methods of the present disclosure can further include separating the alcohol from the aqueous phase. Suitable removal techniques from the aqueous phase can include, for example, solvent washing, azeotropic distillation, and the like.

In some or other embodiments, an alcohol byproduct and/or an alcohol solvent can be separated from the intermediate titanium catechol complex. Separation of the alcohol can be desirable, for example, when one does not want the alcohol to become incorporated in the aqueous phase upon forming the salt form titanium catechol complex. Suitable techniques for removing the alcohol from the intermediate titanium catechol complex can be similar to those described above for removing a hydrogen halide gas byproduct (e.g., reduced pressure, flowing inert gas, and the like). In some instances, an alcohol can be removed through contact of the reaction mixture with an organic solvent in which the alcohol is miscible and which is immiscible with the organic solvent used for forming the intermediate titanium catechol complex.

In other embodiments, an alcohol can be separated from the intermediate titanium catechol complex by isolating the intermediate titanium catechol complex from the reaction mixture, in which case the alcohol is removed with the mother liquor. Suitable techniques for isolating and optionally further purifying the intermediate titanium catechol complex are discussed above.

In some embodiments, a titanium alkoxide can be generated in situ within the reaction mixture. In more particular embodiments, a titanium reagent, such as a titanium tetrahalide, can be reacted with an alcohol solvent to generate the titanium alkoxide in situ and to liberate a hydrogen halide gas as a byproduct. The in situ-generated titanium alkoxide can then react as described above to produce the intermediate titanium catechol complex and to regenerate an alcohol in the reaction mixture. The hydrogen halide byproduct and the alcohol byproduct can be addressed separately or concurrently using the techniques discussed above for removing these byproduct species.

An amount of base in the alkaline aqueous solution can be chosen such that it is sufficient to convert the intermediate titanium catechol complex into its corresponding salt form in an aqueous phase. In particular embodiments, the base can be an alkali metal base or combination of alkali metal bases, optionally in further combination with any of the other bases discussed herein. Accordingly, in some embodiments, the salt form titanium catechol complex can be an alkali metal salt form. The amount of base can be chosen to be stoichiometrically equivalent to that of the titanium reagent initially present, or the base can be present in a slight stoichiometric excess or deficit. Accordingly, the resulting aqueous phase containing the salt form titanium catechol complex can be neutral, modestly basic or modestly acidic, depending upon the actual amount of base that is present and the yield at which the intermediate titanium catechol complex formed. Since the synthetic methods described herein allow various salt-forming byproducts, such as HCl gas and other hydrogen halides, to be substantially removed from the reaction mixture, essentially none of the base is consumed to form unwanted extraneous salts, such as alkali metal chlorides, in the aqueous phase. Further, since the intermediate titanium catechol complex is formed in high yields, a good estimate of the aqueous phase pH can be obtained based upon the initial molar amount of titanium reagent that is present and the molar amount of added base.

In more particular embodiments, an amount of base in the alkaline aqueous solution is such that the aqueous phase containing the salt form titanium catechol complex has a pH of about 6 to about 8. In still more particular embodiments, an amount of the base can be chosen such that the resulting aqueous phase has a pH of about 7 to about 8. Attaining an initial pH that is not far removed from neutral allows the salt form titanium catechol complex to be formed and maintained in the aqueous phase under pH conditions where it is relatively stable. In addition, an initial pH within this range can be readily adjusted upwardly without introducing extraneous salts, such as alkali metal halides, to the aqueous phase, as described hereinafter. That is, by forming an aqueous phase having a near-neutral pH at which the salt form titanium catechol complex is stable, more careful upward pH adjustment can then take place afterward. In contrast, if excess alkaline aqueous solution was added to convert the intermediate titanium catechol complex into the corresponding salt form, the initial pH would be higher. Although the salt form titanium catechol complex might well be stable at this higher pH, the pH could not be lowered with an acid without introducing extraneous salts in the aqueous phase. For example, in the case of an alkali metal base being present in the alkaline aqueous solution, lowering the initial pH with hydrochloric acid would result in the unwanted production of alkali metal chloride salts, such as sodium chloride or potassium chloride, within the aqueous phase, which can be desirable to avoid for the reasons noted above. Accordingly, in some embodiments, the initial pH can be adjusted by adding an additional quantity of the alkaline aqueous solution or a different alkaline aqueous solution to adjust the pH to a range of about 9 to about 10, or about 10 to about 12, or about 12 to about 14. The pH range can be chosen depending upon the particular application in which the aqueous phase is to be employed.

In various embodiments of the present disclosure, the aqueous phase containing the salt form titanium catechol complex can have a concentration of the complex of about 0.5 M or above. In more particular embodiments, the concentration of the salt form titanium catechol complex can range between about 0.5 M and about 2 M, or between about 0.75 M and about 1.5 M or between about 1 M and about 2 M.

Therefore, in some or other various embodiments, the present disclosure provides compositions containing salt form titanium catechol complexes. In more specific embodiments, the compositions described herein can include an aqueous phase, and a salt form titanium catechol complex dissolved in the aqueous phase, such as an alkali metal salt form, in which the composition contains about 0.01 molar equivalents or less of extraneous salts relative to the salt form titanium catechol complex. In more specific embodiments, the aqueous phase can be substantially free of alkali metal halide salts, particularly sodium chloride or potassium chloride. As discussed above, the synthetic processes described hereinabove allow aqueous phases of this type to be readily prepared.

In some embodiments, the aqueous phase can be substantially free of an organic solvent. The organic solvent that is excluded from the aqueous phase can be that which was used in conjunction with forming the intermediate titanium catechol complex. Water-immiscible organic solvents can be readily excluded. Additional distillation can be conducted to remove the organic solvent from the aqueous phase, if needed.

In other embodiments, the aqueous phase formed in accordance with the disclosure above can contain at least some amount of organic solvent. In some embodiments, the aqueous phase can contain trace or non-trace amounts of an organic solvent that was used in conjunction with forming the intermediate titanium catechol complex. In some embodiments, the organic solvent can be a water-miscible aprotic organic solvent that is non-reactive with titanium tetrachloride or other titanium reagents, such as those discussed above. In other embodiments, water-miscible protic solvents, such as alcohols, can become incorporated in the aqueous phase. In some or other embodiments, a quantity of organic solvent can be added to the aqueous phase after its formation. Organic solvents added to the aqueous phase after its formation can include water-miscible organic solvents that are either reactive or non-reactive with titanium tetrachloride or other titanium reagents. In more particular embodiments, alcohol or glycol solvents can be added to the aqueous phase after its formation.

In more specific embodiments, the aqueous phase can contain at least about 98% water by weight. In other more specific embodiments, the aqueous phase can contain at least about 55% water by weight, or at least about 60% water by weight, or at least about 65% water by weight, or at least about 70% water by weight, or at least about 75% water by weight, or at least about 80% water by weight, or at least about 85% water by weight, or at least about 90% water by weight, or at least about 95% water by weight. In some embodiments, the aqueous phase can be free of water-miscible organic solvents and consist of water alone as a solvent for the salt form titanium catechol complex.

In further embodiments, the aqueous phase can include a viscosity modifier, a wetting agent, a buffer, or any combination thereof. Suitable viscosity modifiers can include, for example, corn starch, corn syrup, gelatin, glycerol, guar gum, pectin, and the like. Other suitable examples will be familiar to one having ordinary skill in the art. Suitable wetting agents can include, for example, various non-ionic surfactants and/or detergents. In some or other embodiments, the aqueous phase can further include a glycol or a polyol. Suitable glycols can include, for example, ethylene glycol, diethylene glycol, and polyethylene glycol. Suitable polyols can include, for example, glycerol, mannitol, sorbitol, pentaerythritol, and tris(hydroxymethyl)aminomethane. Illustrative buffers that can be present include, but are not limited to, salts of phosphates, borates, carbonates, silicates, tris(hydroxymethyl)aminomethane (TRIS), 4-(2-hydroxyethyl)-1-piperazineethanesulfonic acid (HEPES), piperazine-N,N'-bis(ethanesulfonic acid) (PIPES), or any combination thereof. Inclusion of any of these components in the aqueous phase can help maintain the alkali metal salt form titanium catechol complex in a dissolved form and/or facilitate the incorporation of the aqueous phase in a flow battery, for example.

In some embodiments, the aqueous phases described herein can further include one or more mobile ions (i.e., an extraneous electrolyte) for use as an electrolyte solution in a flow battery or similar electrochemical system. In some embodiments, suitable mobile ions can include proton, hydronium, or hydroxide. In other various embodiments, mobile ions other than proton, hydronium, or hydroxide can be present, either alone or in combination with proton, hydronium or hydroxide. Such alternative mobile ions can include, for example, alkali metal or alkaline earth metal cations (e.g., $Li^+$, $Na^+$, $K^+$, $Mg^{2+}$, $Ca^{2+}$ and $Sr^{2+}$) and halides (e.g., $F^-$, $Cl^-$, or $Br^-$). Other suitable mobile ions can include, for example, ammonium and tetraalkylammonium ions, chalcogenides, phosphate, hydrogen phosphate, phosphonate, nitrate, sulfate, nitrite, sulfite, perchlorate, tetrafluoroborate, hexafluorophosphate, and any combination thereof. In some embodiments, less than about 50% of the mobile ions can constitute protons, hydronium, or hydroxide. In other various embodiments, less than about 40%, less than about 30%, less than about 20%, less than about 10%, less than about 5%, or less than about 2% of the mobile ions can constitute protons, hydronium, or hydroxide. In other various embodiments, aqueous phases containing the salt form titanium catechol complexes of the present disclosure can lack an extraneous electrolyte altogether.

As indicated above, the salt form titanium catechol complexes of the present disclosure, particularly an alkali metal salt form titanium catechol complex, and related aqueous phases containing these complexes can be incorporated in flow batteries and related electrochemical systems. Further disclosure on suitable flow batteries and their operating parameters follows hereinafter.

In various embodiments, flow batteries of the present disclosure can include a first half-cell having a first electrolyte solution therein, in which the first electrolyte solution is an aqueous phase containing a salt form titanium catechol complex containing about 0.01 molar equivalents or less of extraneous salts relative to the salt form titanium catechol complex. More specific disclosure regarding the salt form titanium catechol complexes is provided above.

In further embodiments, flow batteries of the present disclosure can also include a second half-cell having a second electrolyte solution therein, where the second electrolyte solution contains an active material differing from that in the first electrolyte solution. In more specific embodiments, the second electrolyte solution can be an aqueous solution containing an iron hexacyanide complex. Iron hexacyanide complexes can be particularly desirable active materials due to their facile electrode kinetics and substantially reversible electrochemical behavior within the working electrochemical window of aqueous solutions. Nitroxide compounds (particularly [2,2,6,6-tetramethyl-4-(sulfooxy)piperidin-1-yl]oxidanyl or salt, or a pyrroline, pyrrolidine, imidazoline, imidazolidine, oxazoline, oxazolidine, thiazoline, thioazolidine, and their benzo-fused analogues, and derivatives thereof) can be similarly advantageous active materials for the second electrolyte solution in some embodiments. Hence, these substances can allow high open circuit potentials and cell efficiencies to be realized, particularly in combination with a salt form titanium catechol complex as the active material in the first electrolyte solution. In more specific embodiments, flow batteries of the present disclosure can include the first electrolyte solution in contact with a negative electrode of the flow battery and the second electrolyte solution in contact with the positive electrode of the flow battery.

Illustrative flow battery configurations will now be described in further detail. The flow batteries of the present disclosure are, in some embodiments, suited to sustained charge or discharge cycles of several hour durations. As such, they can be used to smooth energy supply/demand profiles and provide a mechanism for stabilizing intermittent power generation assets (e.g., from renewable energy sources such as solar and wind energy). It should be appreciated, then, that various embodiments of the present disclosure include energy storage applications where such long charge or discharge durations are desirable. For example, in non-limiting examples, the flow batteries of the present disclosure can be connected to an electrical grid to allow renewables integration, peak load shifting, grid firming, baseload power generation and consumption, energy arbitrage, transmission and distribution asset deferral, weak grid support, frequency regulation, or any combination thereof. When not connected to an electrical grid, the flow batteries of the present disclosure can be used as power sources for remote camps, forward operating bases, off-grid telecommunications, remote sensors, the like, and any combination thereof. Further, while the disclosure herein is generally directed to flow batteries, it is to be appreciated that other electrochemical energy storage media can incorporate the aqueous phases described herein, specifically those utilizing stationary electrolyte solutions.

In some embodiments, flow batteries of the present disclosure can include: a first chamber containing a negative electrode contacting a first aqueous electrolyte solution; a second chamber containing a positive electrode contacting a second aqueous electrolyte solution, and a separator disposed between the first and second electrolyte solutions. The first aqueous electrolyte solution can be an aqueous phase containing a salt form titanium catechol complex, as described above. The chambers provide separate reservoirs within the cell, through which the first and/or second electrolyte solutions circulate so as to contact the respective electrodes and the separator. Each chamber and its associated electrode and electrolyte solution define a corresponding half-cell. The separator provides several functions which include, for example, (1) serving as a barrier to mixing of the first and second electrolyte solutions, (2) electrically insulating to reduce or prevent short circuits between the positive and negative electrodes, and (3) to facilitate ion transport between the positive and negative electrolyte chambers, thereby balancing electron transport during charge and discharge cycles. The negative and positive electrodes provide a surface where electrochemical reactions can take place during charge and discharge cycles. During a charge or discharge cycle, electrolyte solutions can be transported from separate storage tanks through the corresponding chambers. In a charging cycle, electrical power can be applied to the cell such that the active material contained in the second electrolyte solution undergoes a one or more electron oxidation and the active material in the first electrolyte solution undergoes a one or more electron reduction. Similarly, in a discharge cycle the second active material is reduced and the first active material is oxidized to generate electrical power.

In more specific embodiments, illustrative flow batteries of the present disclosure can include: (a) a first aqueous electrolyte solution containing a first coordination complex; (b) a second aqueous electrolyte solution containing a second coordination complex or a nitroxide compound; (c) a separator positioned between said first and second aqueous electrolyte solutions; and (d) an optional mobile ion in the first and second aqueous electrolyte solutions. As described in more detail below, the separator can be an ionomer membrane, and it can have a thickness of less than 100 microns and have an associated net charge that is the same sign as that of the first and second coordination complexes.

FIG. 1 depicts a schematic of an illustrative flow battery containing a single electrochemical cell. Although FIG. 1 shows a flow battery containing a single electrochemical cell, approaches for combining multiple electrochemical cells together are known and are discussed in brief hereinbelow. Unlike typical battery technologies (e.g., Li-ion, Ni-metal hydride, lead-acid, and the like), where active materials and other components are housed in a single assembly, flow batteries transport (e.g., via pumping) redox-active energy storage materials from storage tanks through an electrochemical stack. This design feature decouples the electrical energy storage system power from the energy storage capacity, thereby allowing for considerable design flexibility and cost optimization.

As shown in FIG. 1, flow battery 1 includes an electrochemical cell that features separator 20 (e.g., a membrane) that separates the two electrodes 10 and 10' of the electrochemical cell. As used herein, the terms "separator" and "membrane" synonymously refer to an ionically conductive and electrically insulating material disposed between the positive and negative electrodes of an electrochemical cell. Electrodes 10 and 10' are formed from a suitably conductive material, such as a metal, carbon, graphite, and the like. Although FIG. 1 has shown electrodes 10 and 10' as being spaced apart from separator 20, electrodes 10 and 10' can also be abutted with separator 20 in more particular embodiments. The material(s) forming electrodes 10 and 10' can be porous, such that they have a high surface area for contacting first electrolyte solution 30 and second electrolyte solution 40, the active materials of which are capable of cycling between an oxidized state and a reduced state during operation of flow battery 1. For example, one or both of electrodes 10 and 10' can be formed from a porous carbon cloth or a carbon foam in particular embodiments.

Pump 60 affects transport of first electrolyte solution 30 containing a first active material from tank 50 to the electrochemical cell. The flow battery also suitably includes second tank 50' that holds second electrolyte solution 40 containing a second active material. The second active material in second electrolyte solution 40 can be the same material as the first active material in first electrolyte solution 30, or it can be different. Second pump 60' can affect transport of second electrolyte solution 40 to the electrochemical cell. Pumps (not shown in FIG. 1) can also be used to affect transport of the first and second electrolyte solutions 30 and 40 from the electrochemical cell back to tanks 50 and 50'. Other methods of affecting fluid transport, such as siphons, for example, can also suitably transport first and second electrolyte solutions 30 and 40 into and out of the electrochemical cell. Also shown in FIG. 1 is power source or load 70, which completes the circuit of the electrochemical cell and allows a user to collect or store electricity during its operation. Connection to the electrical grid for charging or discharging purposes can also occur at this location.

It should be understood that FIG. 1 depicts a specific, non-limiting embodiment of a flow battery. Accordingly, flow batteries consistent with the spirit of the present disclosure can differ in various aspects relative to the configuration of FIG. 1. As one example, a flow battery system can include one or more active materials that are solids, gases, and/or gases dissolved in liquids. Active materials can be stored in a tank, in a vessel open to the atmosphere, or simply vented to the atmosphere.

During operation of a flow battery in a charging cycle, one of the active materials undergoes oxidation and the other active material undergoes reduction. In a discharging cycle, the opposite processes occur in each half-cell. Upon changing the oxidation states of the active materials, the chemical potentials of the electrolyte solutions are no longer in balance with one another. To relieve the chemical potential imbalance, dissolved mobile ions migrate through the separator to lower the charge in one electrolyte solution and to raise the charge in the other electrolyte solution. Thus, the mobile ions transfer the charge generated upon oxidizing or reducing the active materials, but the mobile ions themselves are not usually oxidized or reduced. To maintain facile electrode kinetics, the flow batteries are configured such that the mobile ions and the active materials remain continuously dissolved in the electrolyte solutions. In addition, by keeping the mobile ions and the active materials continuously dissolved in the electrolyte solutions, potential issues associated with circulating solids can be averted.

As indicated above, multiple electrochemical cells can also be combined with one another in an electrochemical stack in order to increase the rate that energy can be stored and released during operation. The amount of energy released is determined by the overall amount of active materials that are present. An electrochemical stack utilizes bipolar plates between adjacent electrochemical cells to establish electrical communication but not fluid communication between the two cells across the bipolar plate. Thus, bipolar plates contain the electrolyte solutions in an appropriate half-cell within the individual electrochemical cells. Bipolar plates are generally fabricated from electrically conductive materials that are fluidically non-conductive on the whole. Suitable materials can include carbon, graphite, metal, or a combination thereof. Bipolar plates can also be fabricated from non-conducting polymers having a conductive material dispersed therein, such as carbon particles or fibers, metal particles or fibers, graphene, and/or carbon nanotubes. Although bipolar plates can be fabricated from the same types of conductive materials as can the electrodes of an electrochemical cell, they can lack the continuous porosity permitting an electrolyte solution to flow completely through the latter. It should be recognized that bipolar plates are not necessarily entirely non-porous entities, however. Bipolar plates can have innate or designed flow channels that provide a greater surface area for allowing an electrolyte solution to contact the bipolar plate. Suitable flow channel configurations can include, for example, interdigitated flow channels. In some embodiments, the flow channels can be used to promote delivery of an electrolyte solution to an electrode within the electrochemical cell.

In some instances, an electrolyte solution can be delivered to and withdrawn from each electrochemical cell via a fluid inlet manifold and a fluid outlet manifold (not shown in FIG. 1). In some embodiments, the fluid inlet manifold and the fluid outlet manifold can provide and withdraw an electrolyte solution via the bipolar plates separating adjacent electrochemical cells. Separate manifolds can provide each electrolyte solution individually to the two half-cells of each electrochemical cell. In more particular embodiments, the fluid inlet manifold and the fluid outlet manifold can be configured to supply and withdraw the electrolyte solutions via opposing lateral faces of the bipolar plates (e.g. by supplying and withdrawing the electrolyte solution from opposing ends of the flow channels of the bipolar plate).

As used herein, the terms "separator" and "membrane" refer to an ionically conductive and electrically insulating, material disposed between the positive and negative electrodes of an electrochemical cell. The separator can be a porous membrane in some embodiments and/or an ionomer membrane in other various embodiments. In some embodiments, the separator can be formed from an ionically conductive polymer.

Polymer membranes can be anion- or cation-conducting electrolytes. Where described as an "ionomer," the term refers to polymer membrane containing both electrically neutral repeating units and ionized repeating units, where the ionized repeating units are pendant and covalently bonded to the polymer backbone. In general, the fraction of ionized units can range from about 1 mole percent to about 90 mole percent. For example, in some embodiments, the content of ionized units is less than about 15 mole percent; and in other embodiments, the ionic content is higher, such as greater than about 80 mole percent. In still other embodiments, the ionic content is defined by an intermediate range, for example, in a range of about 15 to about 80 mole percent. Ionized repeating units in an ionomer can include anionic functional groups such as sulfonate, carboxylate, and the like. These functional groups can be charge balanced by, mono-, di-, or higher-valent cations, such as alkali or alkaline earth metals. Ionomers can also include polymer compositions containing attached or embedded quaternary ammonium, sulfonium, phosphazenium, and guanidinium residues or salts. Suitable examples will be familiar to one having ordinary skill in the art.

In some embodiments, polymers useful as a separator can include highly fluorinated or perfluorinated polymer backbones. Certain polymers useful in the present disclosure can include copolymers of tetrafluoroethylene and one or more fluorinated, acid-functional co-monomers, which are commercially available as NAFION™ perfluorinated polymer electrolytes from DuPont. Other useful perfluorinated polymers can include copolymers of tetrafluoroethylene and $FSO_2$—$CF_2CF_2CF_2CF_2$—O—$CF$=$CF_2$, FLEMION™ and SELEMION™.

Additionally, substantially non-fluorinated membranes that are modified with sulfonic acid groups (or cation exchanged sulfonate groups) can also be used. Such membranes can include those with substantially aromatic backbones such as, for example, polystyrene, polyphenylene, biphenyl sulfone (BPSH), or thermoplastics such as polyetherketones and polyethersulfones.

Battery-separator style porous membranes, can also be used as the separator. Because they contain no inherent ionic conduction capabilities, such membranes are typically impregnated with additives in order to function. These membranes typically contain a mixture of a polymer and inorganic filler, and open porosity. Suitable polymers can include, for example, high density polyethylene, polypropylene, polyvinylidene difluoride (PVDF), or polytetrafluoroethylene (PTFE). Suitable inorganic fillers can include silicon carbide matrix material, titanium dioxide, silicon dioxide, zinc phosphide, and ceria.

Separators can also be formed from polyesters, polyetherketones, poly(vinyl chloride), vinyl polymers, and substituted vinyl polymers. These can be used alone or in combination with any previously described polymer.

Porous separators are non-conductive membranes which allow charge transfer between two electrodes via open channels filled with electrolyte. The permeability increases the probability of chemicals (e.g., active materials) passing through the separator from one electrode to another and causing cross-contamination and/or reduction in cell energy efficiency. The degree of this cross-contamination can depend on, among other features, the size (the effective diameter and channel length), and character (hydrophobicity/hydrophilicity) of the pores, the nature of the electrolyte, and the degree of wetting between the pores and the electrolyte.

The pore size distribution of a porous separator is generally sufficient to substantially prevent the crossover of active materials between the two electrolyte solutions. Suitable porous membranes can have an average pore size distribution of between about 0.001 nm and 20 micrometers, more typically between about 0.001 nm and 100 nm. The size distribution of the pores in the porous membrane can be substantial. In other words, a porous membrane can contain a first plurality of pores with a very small diameter (approximately less than 1 nm) and a second plurality of pores with a very large diameter (approximately greater than 10 micrometers). The larger pore sizes can lead to a higher amount of active material crossover. The ability for a porous membrane to substantially prevent the crossover of active materials can depend on the relative difference in size between the average pore size and the active material. For example, when the active material is a metal center in a coordination complex, the average diameter of the coordination complex can be about 50% greater than the average pore size of the porous membrane. On the other hand, if a porous membrane has substantially uniform pore sizes, the average diameter of the coordination complex can be about 20% larger than the average pore size of the porous membrane. Likewise, the average diameter of a coordination complex is increased when it is further coordinated with at least one water molecule. The diameter of a coordination complex of at least one water molecule is generally considered to be the hydrodynamic diameter. In such embodiments, the hydrodynamic diameter is generally at least about 35% greater than the average pore size. When the average pore size is substantially uniform, the hydrodynamic radius can be about 10% greater than the average pore size.

In some embodiments, the separator can also include reinforcement materials for greater stability. Suitable reinforcement materials can include nylon, cotton, polyesters, crystalline silica, crystalline titania, amorphous silica, amorphous tiania, rubber, asbestos, wood or any combination thereof.

Separators within the flow batteries of the present disclosure can have a membrane thickness of less than about 500 micrometers, or less than about 300 micrometers, or less than about 250 micrometers, or less than about 200 micrometers, or less than about 100 micrometers, or less than about 75 micrometers, or less than about 50 micrometers, or less than about 30 micrometers, or less than about 25 micrometers, or less than about 20 micrometers, or less than about 15 micrometers, or less than about 10 micrometers. Suitable separators can include those in which the flow battery is capable of operating with a current efficiency of greater than about 85% with a current density of 100 mA/cm$^2$ when the separator has a thickness of 100 micrometers. In further embodiments, the flow battery is capable of operating at a current efficiency of greater than 99.5% when the separator has a thickness of less than about 50 micrometers, a current efficiency of greater than 99% when the separator has a thickness of less than about 25 micrometers, and a current efficiency of greater than 98% when the separator has a thickness of less than about 10 micrometers. Accordingly, suitable separators include those in which the flow battery is capable of operating at a voltage efficiency of greater than 60% with a current density of 100 mA/cm$^2$. In further embodiments, suitable separators can include those in which the flow battery is capable of operating at a voltage efficiency of greater than 70%, greater than 80% or even greater than 90%.

The diffusion rate of the first and second active materials through the separator can be less than about $1\times10^{-5}$ mol cm$^{-2}$ day$^{-1}$, or less than about $1\times10^{-6}$ mol cm$^{-2}$ day$^{-1}$, or less than about $1\times10^{-7}$ mol cm$^{-2}$ day$^{-1}$, or less than about $1\times10^{-9}$ mol cm$^{-2}$ day$^{-1}$, or less than about $1\times10^{-11}$ mol cm$^{-2}$ day$^{-1}$, or less than about $1\times10^{-13}$ mol cm$^{-2}$ day$^{-1}$, or less than about $1\times10^{-15}$ mol cm$^{-2}$ day$^{-1}$.

The flow batteries can also include an external electrical circuit in electrical communication with the first and second electrodes. The circuit can charge and discharge the flow battery during operation. Reference to the sign of the net ionic charge of the first, second, or both active materials relates to the sign of the net ionic charge in both oxidized and reduced forms of the redox active materials under the conditions of the operating flow battery. Further exemplary embodiments of a flow battery provide that (a) the first active material has an associated net positive or negative charge and is capable of providing an oxidized or reduced form over an electric potential in a range of the negative operating potential of the system, such that the resulting oxidized or reduced form of the first active material has the same charge sign (positive or negative) as the first active material and the ionomer membrane also has a net ionic charge of the same sign; and (b) the second active material has an associated net positive or negative charge and is capable of providing an oxidized or reduced form over an electric potential in a range of the positive operating potential of the system, such that the resulting oxidized or reduced form of the second active material has the same charge sign (positive or negative sign) as the second active material and the ionomer membrane also has a net ionic charge of the same sign; or both (a) and (b). In some embodiments, the net ionic charge in both the oxidized and reduced forms can be negative. The matching charges of the first and/or second active materials and the ionomer membrane can provide a high selectivity. More specifically, charge matching can provide less than about 3%, less than about 2%, less than about 1%, less than about 0.5%, less than about 0.2%, or less than about 0.1% of the molar flux of ions passing through the ionomer membrane as being attributable to the first or second active material. The term "molar flux of ions" refers to the amount of ions passing through the ionomer membrane, balancing the charge associated with the flow of external electricity/electrons. That is, the flow battery is capable of operating or operates with the substantial exclusion of the active materials by the ionomer membrane, and such exclusion can be promoted through charge matching.

Flow batteries incorporating the electrolyte solutions of the present disclosure can have one or more of the following operating characteristics: (a) where, during the operation of the flow battery, the first or second active materials comprise less than about 3% of the molar flux of ions passing through the ionomer membrane, (b) where the round trip current efficiency is greater than about 70%, greater than about 80%, or greater than about 90%; (c) where the round trip current efficiency is greater than about 90%; (d) where the sign of the net ionic charge of the first, second, or both active materials is the same in both oxidized and reduced forms of the active materials and matches that of the ionomer membrane; (e) where the ionomer membrane has a thickness of less than about 100 µm, less than about 75 µm, less than about 50 µm, or less than about 250 µm; (f) where the flow battery is capable of operating at a current density of greater than about 100 mA/cm² with a round trip voltage efficiency of greater than about 60%; and (g) where the energy density of the electrolyte solutions is greater than about 10 Wh/L, greater than about 20 Wh/L, or greater than about 30 Wh/L.

In some cases, a user may desire to provide higher charge or discharge voltages than available from a single battery cell. In such cases, several battery cells can be connected in series such that the voltage of each cell is additive. This forms a bipolar stack. An electrically conductive, but non-porous material (e.g., a bipolar plate) can be employed to connect adjacent battery cells in a bipolar stack, which allows for electron transport but prevents fluid or gas transport between adjacent cells. The positive electrode compartments and negative electrode compartments of individual cells can be fluidically connected via common positive and negative fluid manifolds in the stack. In this way, individual cells can be stacked in series to yield a voltage appropriate for DC applications or conversion to AC applications.

In additional embodiments, the cells, cell stacks, or batteries can be incorporated into larger energy storage systems, suitably including piping and controls useful for operation of these large units. Piping, control, and other equipment suitable for such systems are known in the art, and can include, for example, piping and pumps in fluid communication with the respective chambers for moving electrolyte solutions into and out of the respective chambers and storage tanks for holding charged and discharged electrolytes. The cells, cell stacks, and batteries of this disclosure can also include an operation management system. The operation management system can be any suitable controller device, such as a computer or microprocessor, and can contain logic circuitry that sets operation of any of the various valves, pumps, circulation loops, and the like.

In more specific embodiments, a flow battery system can include a flow battery (including a cell or cell stack); storage tanks and piping for containing and transporting the electrolyte solutions; control hardware and software (which may include safety systems); and a power conditioning unit. The flow battery cell stack accomplishes the conversion of charging and discharging cycles and determines the peak power. The storage tanks contain the positive and negative active materials, such as the coordination complexes disclosed herein, and the tank volume determines the quantity of energy stored in the system. The control software, hardware, and optional safety systems suitably include sensors, mitigation equipment and other electronic/hardware controls and safeguards to ensure safe, autonomous, and efficient operation of the flow battery system. A power conditioning unit can be used at the front end of the energy storage system to convert incoming and outgoing power to a voltage and current that is optimal for the energy storage system or the application. For the example of an energy storage system connected to an electrical grid, in a charging cycle the power conditioning unit can convert incoming AC electricity into DC electricity at an appropriate voltage and current for the cell stack. In a discharging cycle, the stack produces DC electrical power and the power conditioning unit converts it to AC electrical power at the appropriate voltage and frequency for grid applications.

Where not otherwise defined hereinabove or understood by one having ordinary skill in the art, the definitions in the following paragraphs will be applicable to the present disclosure.

As used herein, the term "energy density" refers to the amount of energy that can be stored, per unit volume, in the active materials. Energy density refers to the theoretical energy density of energy storage and can be calculated by Equation 1:

$$\text{Energy density} = (26.8 \text{ A-h/mol}) \times OCV \times [e^-] \quad \text{(Equation 1)}$$

where OCV is the open circuit potential at 50% state of charge, (26.8 A-h/mol) is Faraday's constant, and $[e^-]$ is the concentration of electrons stored in the active material at 99% state of charge. In the case that the active materials largely are an atomic or molecular species for both the positive and negative electrolyte, $[e^-]$ can be calculated by Equation 2 as:

$$[e^-] = [\text{active materials}] \times N/2 \quad \text{(Equation 2)}$$

where [active materials] is the molar concentration of the active material in either the negative or positive electrolyte, whichever is lower, and N is the number of electrons transferred per molecule of active material. The related term "charge density" refers to the total amount of charge that each electrolyte contains. For a given electrolyte, the charge density can be calculated by Equation 3

$$\text{Charge density} = (26.8 \text{ A-h/mol}) \times [\text{active material}] \times N \quad \text{(Equation 3)}$$

where [active material] and N are as defined above.

As used herein, the term "current density" refers to the total current passed in an electrochemical cell divided by the geometric area of the electrodes of the cell and is commonly reported in units of mA/cm².

As used herein, the term "current efficiency" ($I_{eff}$) can be described as the ratio of the total charge produced upon discharge of a cell to the total charge passed during charging. The current efficiency can be a function of the state of charge of the flow battery. In some non-limiting embodiments, the current efficiency can be evaluated over a state of charge range of about 35% to about 60%.

As used herein, the term "voltage efficiency" can be described as the ratio of the observed electrode potential, at a given current density, to the half-cell potential for that electrode (×100%). Voltage efficiencies can be described for a battery charging step, a discharging step, or a "round trip voltage efficiency." The round trip voltage efficiency ($V_{eff,rt}$) at a given current density can be calculated from the cell voltage at discharge ($V_{discharge}$) and the voltage at charge ($V_{charge}$) using equation 4:

$$V_{eff,RT} = V_{discharge}/V_{charge} \times 100\%$$ (Equation 4)

As used herein, the terms "negative electrode" and "positive electrode" are electrodes defined with respect to one another, such that the negative electrode operates or is designed or intended to operate at a potential more negative than the positive electrode (and vice versa), independent of the actual potentials at which they operate, in both charging and discharging cycles. The negative electrode may or may not actually operate or be designed or intended to operate at a negative potential relative to a reversible hydrogen electrode. The negative electrode is associated with a first electrolyte solution and the positive electrode is associated with a second electrolyte solution, as described herein. The electrolyte solutions associated with the negative and positive electrodes may be described as negolytes and posolytes, respectively.

EXAMPLES

Standard laboratory procedures intended to exclude ambient atmosphere were followed in the syntheses described herein.

Example 1: Synthesis of NaKTi(Catechol)$_3$

An oven-dried 5 L roundbottom flask was equipped with an overhead stirrer, condenser and septa. A moderate flow of nitrogen gas was then flowed through the system to purge the environment in the flask. The nitrogen outlet was placed at the top of the condenser and was connected to a base trap containing 150 g NaOH in 1 L of water.

To the flask was then added 600 mL of o-xylene, followed by 298.25 g (2.708 mol, 2.97 molar equivalents) of catechol. Stirring was started and an additional 100 mL of o-xylene was then added. The mixture was then heated until the catechol dissolved at a temperature of about 75° C.-80° C. The reaction was maintained at this temperature while adding TiCl$_4$.

In a separate flask, 100 mL of o-xylene was degassed by sparging with nitrogen gas. Into a tared, oven-dried 500 mL amber bottle fitted with a septum was transferred 173 g TiCl$_4$ (100 mL; 0.912 mol, 1.0 molar equivalents), and the degassed o-xylene was transferred to the amber bottle via a cannula. The TiCl$_4$ dissolved in the o-xylene to produce a dark solution. The TiCl$_4$ solution was then added dropwise via cannula to the heated catechol solution. Vigorous reaction occurred in some instances as the initial drops of the TiCl$_4$ solution were added. During the addition over about 2 hours, the reaction mixture turned dark red and then dark brown, and HCl was evolved from the reaction mixture. Solids formed in the reaction mixture during addition of the TiCl$_4$ solution.

After the addition of the TiCl$_4$ solution was complete, the temperature was raised to 120° C., and stirring was then maintained for 17 hours. The nitrogen flow was maintained at a rate sufficient to carry HCl vapors from the flask without substantially removing the o-xylenes solvent.

After the 17-hour heating period was complete, a check for HCl evolution at the nitrogen outlet was conducted with wet pH paper. As a second check that HCl evolution was complete, the nitrogen outlet tube was bubbled into a small quantity of deionized water, and the pH was checked to confirm that the water was non-acidic.

After confirming that HCl evolution was complete, an alkaline aqueous solution was added to the reaction mixture. Specifically, the alkaline aqueous solution was prepared by dissolving 35.57 g NaOH (0.889 mol, 0.975 molar equivalents) and 58.7 g KOH (0.889 mol, 0.975 molar equivalent) in 600 mL of deionized water, followed by degassing with nitrogen sparge for at least 1 hour. The alkaline aqueous solution was then added dropwise to the heated reaction via cannula over 1 hour. Stirring was maintained following the transfer, and the combined reaction mixture was then refluxed for a further three hours.

Following the 3-hour reflux, an aliquot of the resulting aqueous phase was withdrawn, and its pH was determined to be 7.52. A solution containing 4.33 g Na$_4$EDTA (0.0114 mol, 0.0125 molar equivalents), 5.04 g K$_3$EDTA (0.0114 mol, 0.0125 molar equivalents), 0.46 g NaOH (0.0114 mol, 0.0125 molar equivalents) and 1.51 g KOH (0.0228 mol, 0.0250 molar equivalents) dissolved in 100 mL deionized water was then added dropwise over 1 hour to the reaction. The reaction mixture was refluxed for an additional hour, and an aliquot of the aqueous phase was again withdrawn. Following introduction of the additional bases, the pH of the aqueous phase was measured at 10.10.

The reaction mixture was then cooled to about 60° C. and filtered while hot through a coarse fritted glass funnel. The filtrate was then collected and re-filtered through a medium fritted glass funnel. The filtrate layers were then allowed to partition in a separatory funnel while cooling to room temperature. The lower aqueous phase was then collected and further analyses were conducted. The experimentally determined concentration for the alkali metal salt form titanium catechol complex was 0.87 M, providing a yield of 92%. Experimental data for the aqueous phase containing the complex will be presented below for a larger scale synthesis.

Example 2: Synthesis of NaKTi(Catechol)$_3$ at a 72 L Scale

A 72 L roundbottom glass reactor was equipped with a mechanical stirrer, condenser, and 1 L addition funnel. A moderate flow of nitrogen gas (7 L/min) was then flowed through the system. The nitrogen outlet was connected to a base trap.

To the flask was then added 8.621 kg of catechol (78.290 mol, 2.95 molar equivalents) and 20 L of xylenes. Stirring was started, and an additional 5 L of xylenes was then added. The mixture was heated until the catechol dissolved at a temperature of about 75° C.-80° C. The reaction was then maintained at this temperature while adding TiCl$_4$.

To the addition funnel was added 5.041 kg of neat TiCl$_4$ (2.914 L; 26.576 mol, 1.00 molar equivalent) via a cannula. The TiCl$_4$ solution was then added dropwise to the heated catechol solution at a rate of about 6 mL/min over about 8 hours. The reaction mixture was heated at 60° C. for 12 hours under nitrogen flow and then for a further 12 hours at 60° C. at a pressure of 120 torr. The nitrogen purge was discontinued during the vacuum heating step. The base trap was titrated to determine the amount of HCl gas released, ensuring the amount was near theoretical levels (>99% of theoretical HCl released), and additional monitoring was conducted as above to ensure that HCl release was complete. After the vacuum heating step was completed, the nitrogen purge was resumed.

The reactor was then heated to 80° C. and placed under a flowing nitrogen purge. To the reaction mixture was then added 18.75 L of a 3 M alkaline aqueous solution containing equimolar amounts of NaOH and KOH (1.03 kg NaOH and 1.579 kg KOH, each 25.701 mol, 0.975 molar equivalents) over a 2.5-hour addition time. The NaOH/KOH solution was spared with nitrogen before use. The pH of the resulting aqueous phase was then adjusted by adding an additional 0.12 equivalents of NaOH and KOH to the reaction mixture (3 M solution of equimolar NaOH and KOH). Once a stable pH of 9-10 was attained, stirring was stopped to allow the phases to separate. The actual final pH of the aqueous phase was 9.87. The lower aqueous phase was siphoned from the reactor and hot filtered via centrifuge through an aqueous Celite 577 cake containing 262 grams of filtering agent. An emulsion in the residual organic phase in the reactor was also allowed to settle during this time, and additional centrifugation was conducted to obtain a further quantity of aqueous phase, which was combined with the initially separated aqueous phase.

Figure 2A:
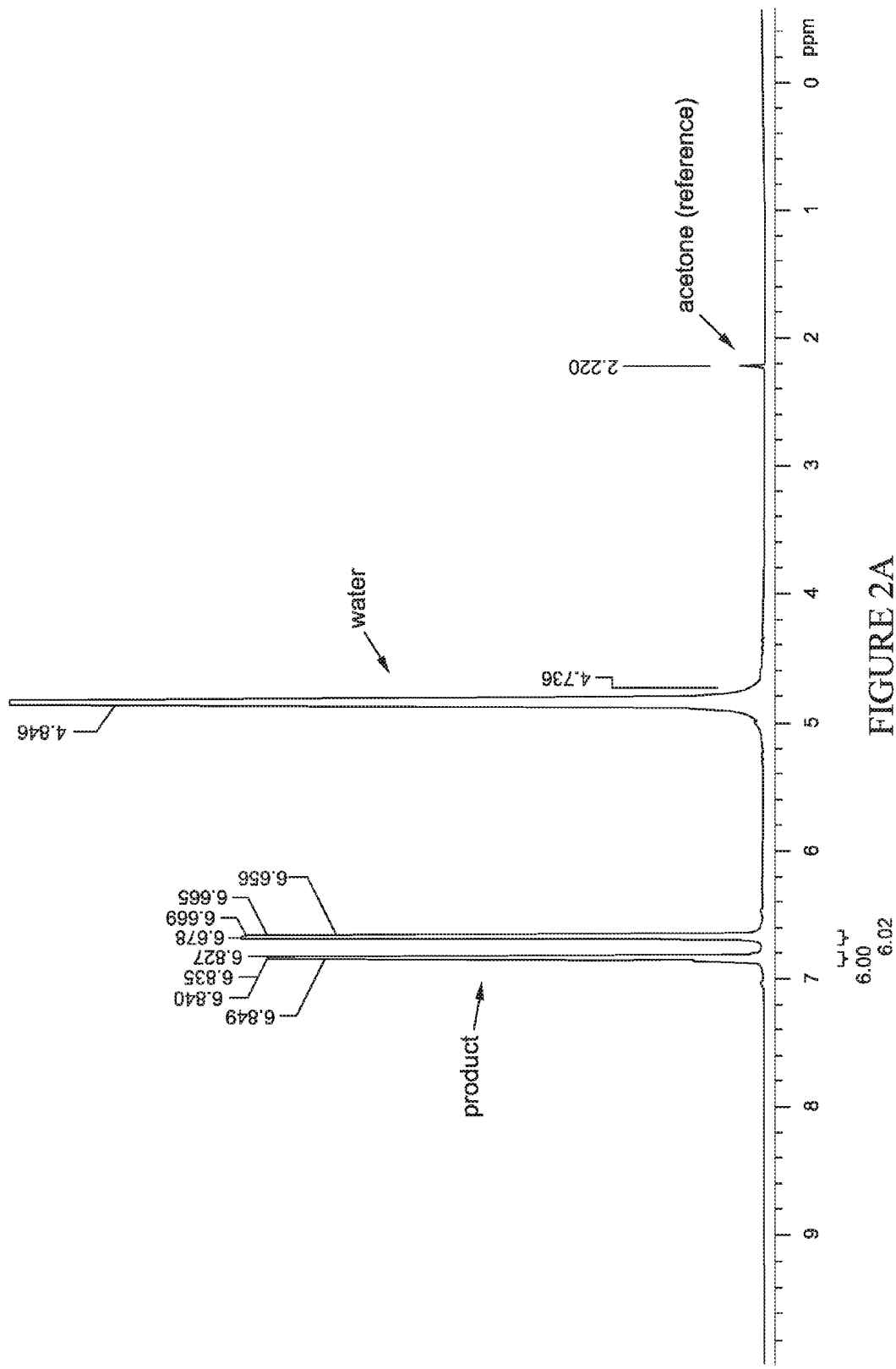
FIGS. 2A and 2B show illustrative $^1$H NMR spectra for the NaKTi(catechol)$_3$ complex in D$_2$O against an acetone reference.
Figure 2B:
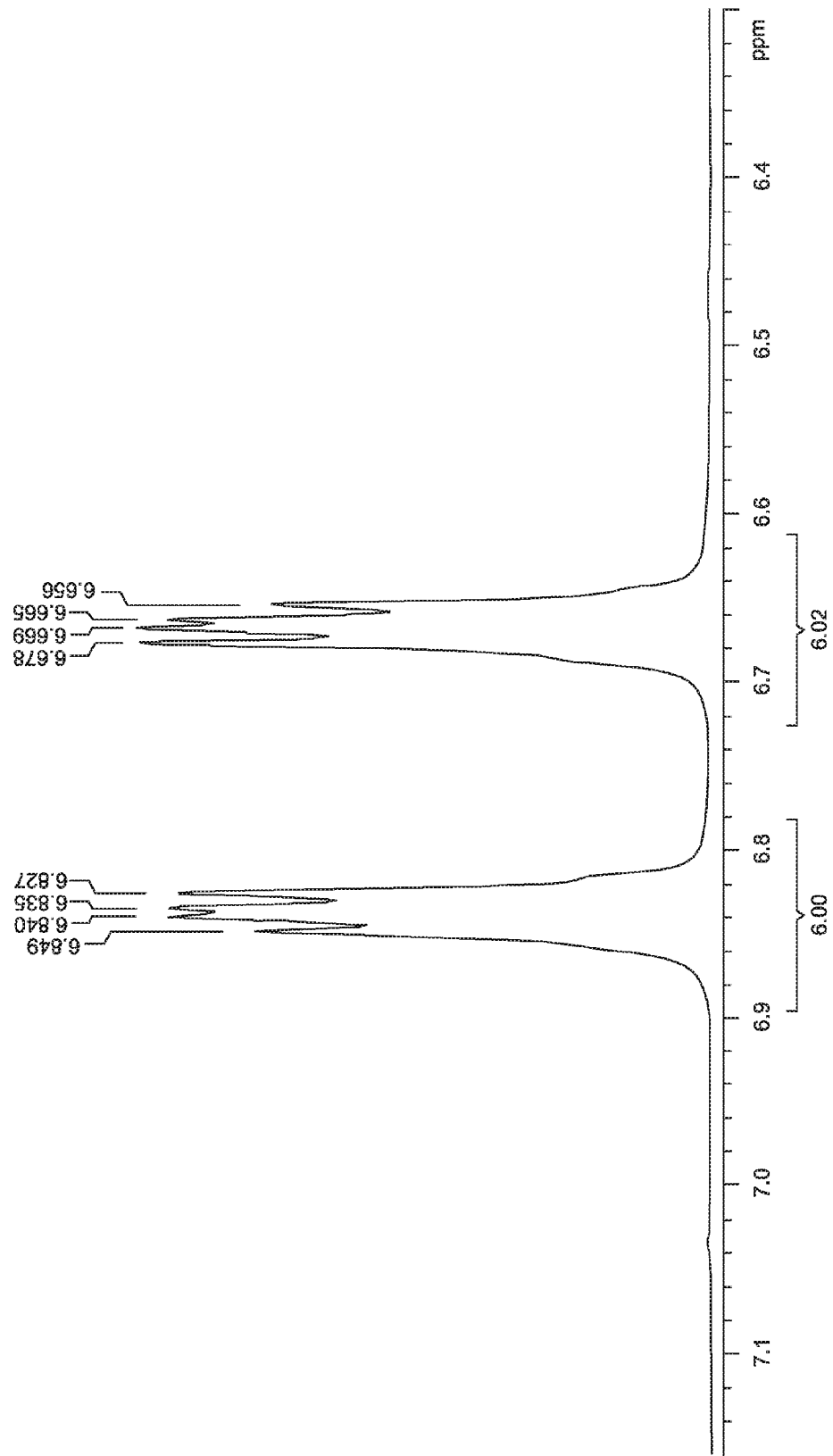
Figure 3A:
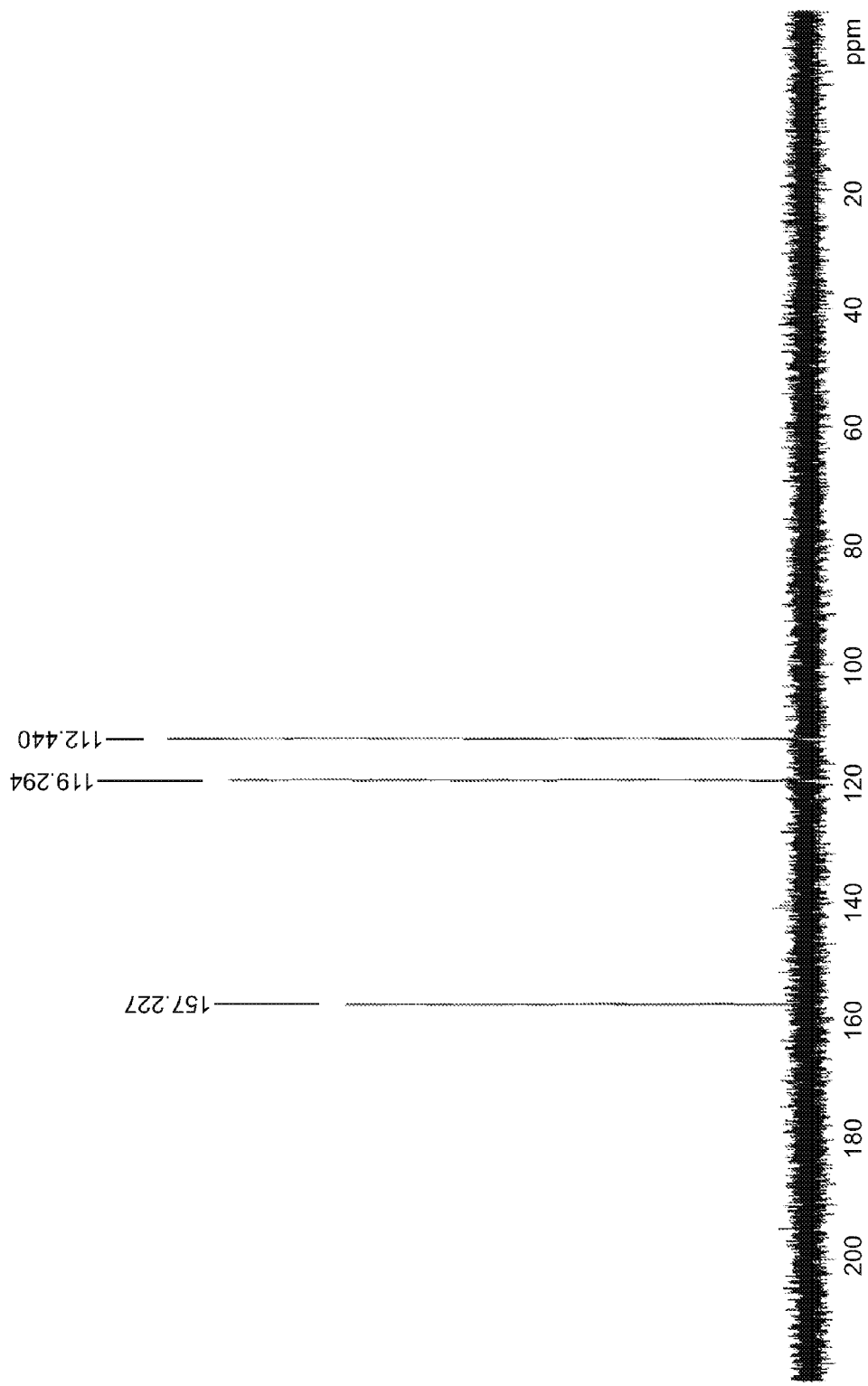
FIGS. 3A and 3B show illustrative $^{13}$C NMR spectra for the NaKTi(catechol)$_3$ complex in D$_2$O.
Figure 3B:
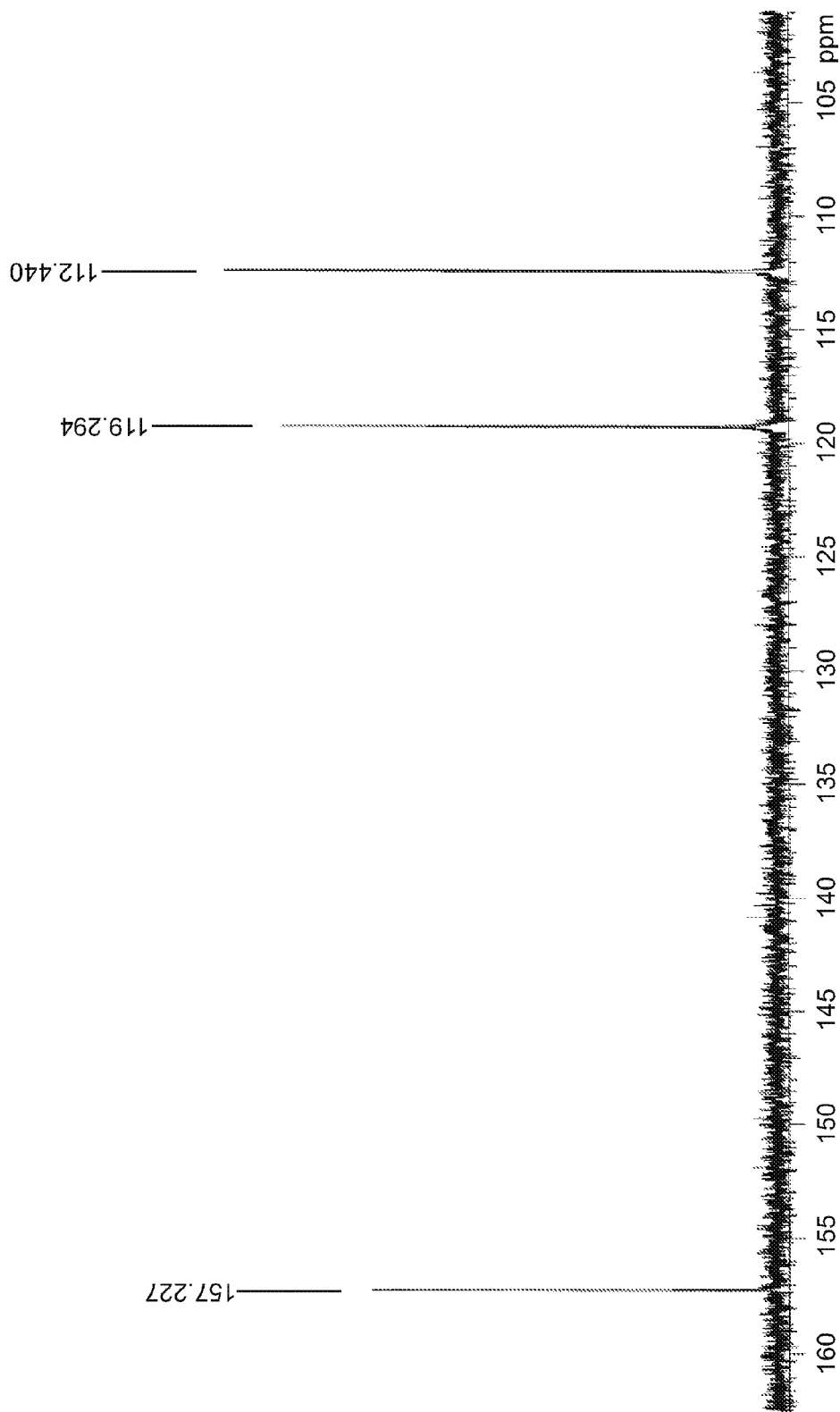
Figure 4:
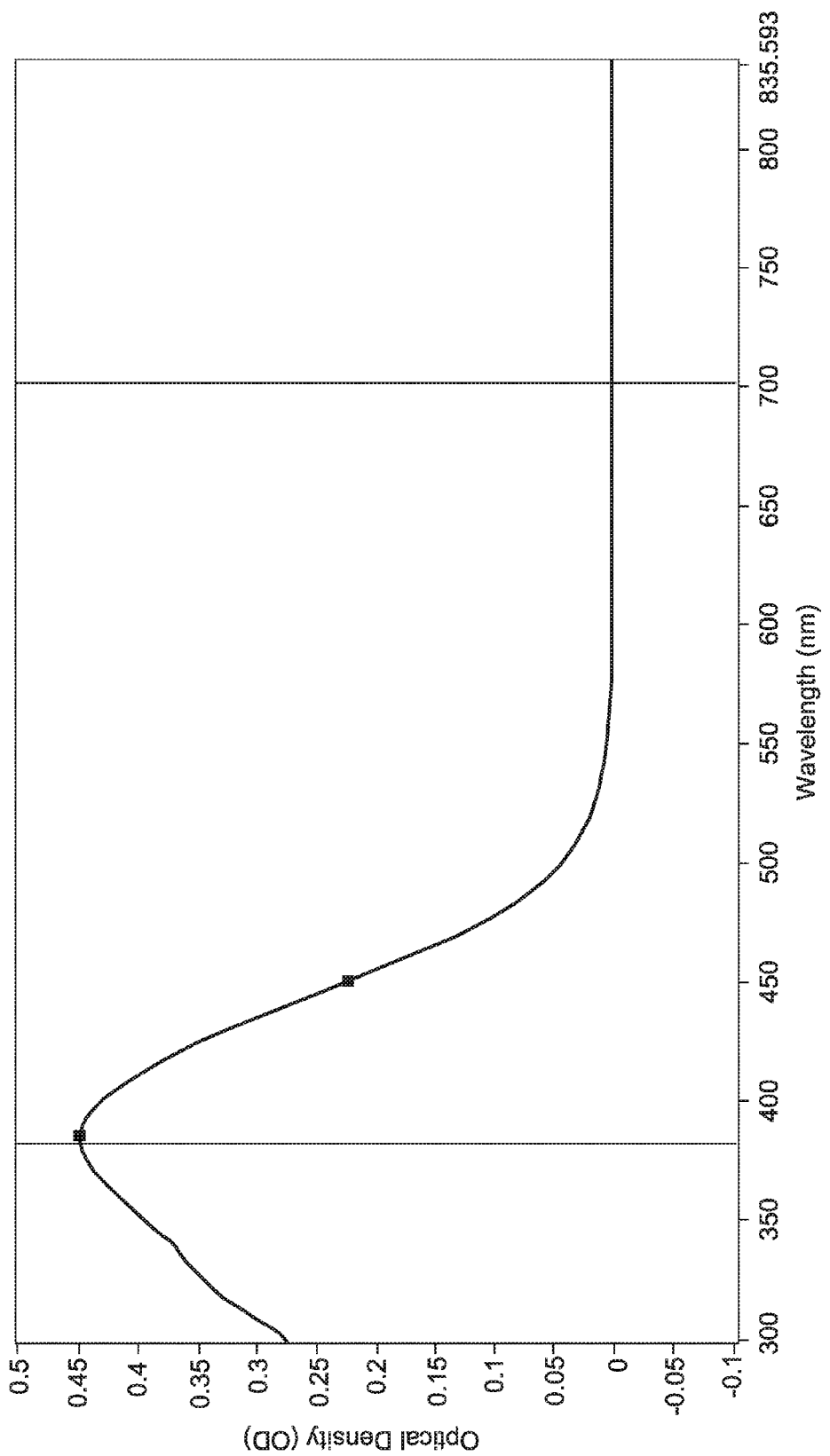
FIG. 4 shows an illustrative UV-VIS spectrum of the NaKTi(catechol)$_3$ complex in water.

The total volume of the aqueous phase collected following filtration was 25.5 L, and the concentration of the alkali metal salt form titanium catechol complex was measured at 0.84 M using UV-VIS spectroscopy. Based on the measured concentration and collected volume, the yield was 82%. Free catechol was undetectable by $^1$H NMR. The aqueous phase was dark red and clear following its isolation. FIGS. 2A and 2B show illustrative $^1$H NMR spectra for the NaKTi(catechol)$_3$ complex in D$_2$O against an acetone reference. FIGS. 3A and 3B show illustrative $^{13}$C NMR spectra for the NaKTi(catechol)$_3$ complex in D$_2$O. FIG. 4 shows an illustrative UV-VIS spectrum of the NaKTi(catechol)$_3$ complex in water.

Although the disclosure has been described with reference to the disclosed embodiments, those skilled in the art will readily appreciate that these are only illustrative of the disclosure. It should be understood that various modifications can be made without departing from the spirit of the disclosure. The disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description.

What is claimed is the following:

1. A method comprising:
    forming a catechol solution comprising a catechol compound and an organic solvent;
    contacting a titanium reagent with the catechol solution to form a reaction mixture;
    reacting the titanium reagent with the catechol compound to form an intermediate titanium catechol complex and a byproduct species;
    separating the byproduct species from the intermediate titanium catechol complex; and
    combining an alkaline aqueous solution with the intermediate titanium catechol complex, the alkaline aqueous solution comprising a base;
    wherein the base converts the intermediate titanium catechol complex into a salt form titanium catechol complex that is at least partially dissolved in an aqueous phase.

2. The method of claim 1, wherein the base comprises an alkali metal base.

3. The method of claim 2, wherein the alkali metal base comprises an alkali metal hydroxide.

4. The method of claim 2, wherein the base further comprises an ammonium base.

5. The method of claim 1, wherein the titanium reagent is selected from the group consisting of titanium tetrachloride, titanium tetrabromide, titanium tetraiodide, a titanium mixed tetrahalide, titanium oxychloride, titanium oxybromide, titanium oxyiodide, titanium oxysulfate, and a titanium alkoxide.

6. The method of claim 5, wherein the byproduct species comprises one or more hydrogen halides.

7. The method of claim 6, wherein the byproduct species is separated from the intermediate titanium catechol complex by maintaining the reaction mixture at reduced pressure, contacting the reaction mixture with a flowing inert gas, or any combination thereof before combining the alkaline aqueous solution with the intermediate titanium catechol complex.

8. The method of claim 6, wherein the intermediate titanium catechol complex is isolated from the reaction mixture to separate the byproduct species from the intermediate titanium catechol complex before combining the alkaline aqueous solution with the intermediate titanium catechol complex.

9. The method of claim 5, wherein the byproduct species comprises sulfuric acid.

10. The method of claim 9, wherein the intermediate titanium catechol complex is isolated from the reaction mixture to separate the byproduct species from the intermediate titanium catechol complex before combining the alkaline aqueous solution with the intermediate titanium catechol complex.

11. The method of claim 9, wherein the byproduct species is separated from the intermediate titanium catechol complex by contacting the reaction mixture with a solvent in which the sulfuric acid is miscible but the intermediate titanium catechol complex is not, the solvent in which the sulfuric acid is miscible also being immiscible with the organic solvent comprising the reaction mixture.

12. The method of claim 5, wherein the byproduct species comprises an alcohol.

13. The method of claim 12, wherein the byproduct species is separated from the intermediate titanium catechol complex by maintaining the reaction mixture at reduced pressure, contacting the reaction mixture with a flowing inert gas, or any combination thereof before combining the alkaline aqueous solution with the intermediate titanium catechol complex.

14. The method of claim 12, wherein the intermediate titanium catechol complex is isolated from the reaction mixture to separate the byproduct species from the intermediate titanium catechol complex before combining the alkaline aqueous solution with the intermediate titanium catechol complex.

15. The method of claim 12, wherein the byproduct species is separated from the intermediate titanium catechol complex by contacting the reaction mixture with a solvent in which the alcohol is miscible but the intermediate titanium catechol complex is not, the solvent in which the alcohol is miscible also being immiscible with the organic solvent comprising the reaction mixture.

16. The method of claim 1, wherein the organic solvent comprises a water-immiscible organic solvent.

17. The method of claim 16, wherein the water-immiscible organic solvent is selected from the group consisting of toluene, xylenes, cyclohexane, dichloromethane, dichloroethane, and any combination thereof.

18. The method of claim 1, wherein an amount of base in the alkaline aqueous solution is such that the aqueous phase containing the salt form titanium catechol complex has a pH of from about 6 to about 8.

19. The method of claim 18, further comprising adding an additional quantity of the alkaline aqueous solution or a different alkaline aqueous solution to the aqueous phase to adjust the pH of the aqueous phase to a range of from about 9 to about 10.

20. The method of claim 1, wherein the intermediate titanium catechol complex and the salt form titanium catechol complex are formed consecutively in a single reaction vessel.

21. The method of claim 1, further comprising separating the aqueous phase and an organic phase from one another, the organic phase comprising the organic solvent.

22. A method comprising:
    forming a catechol solution comprising a catechol compound and an organic solvent;
    contacting a titanium alkoxide with the catechol solution to form a reaction mixture;
    reacting the titanium alkoxide with the catechol compound to form an intermediate titanium catechol complex and an alcohol; and
    without separating the intermediate titanium catechol complex from the alcohol, combining an alkaline aqueous solution with the intermediate titanium catechol complex, the alkaline aqueous solution comprising a base;
    wherein the base converts the intermediate titanium catechol complex into a salt form titanium catechol complex that is at least partially dissolved in an aqueous phase further comprising the alcohol.

23. The method of claim 22, further comprising separating the alcohol from the aqueous phase.

\* \* \* \* \*

UNITED STATES PATENT AND TRADEMARK OFFICE
CERTIFICATE OF CORRECTION

PATENT NO. : 10,377,687 B2
APPLICATION NO. : 15/436716
DATED : August 13, 2019
INVENTOR(S) : Millard et al.

It is certified that error appears in the above-identified patent and that said Letters Patent is hereby corrected as shown below:

On the Title Page

Item [56], References Cited, under heading OTHER PUBLICATIONS:

Replace "CEROFONTAIN et al. "Sulfonation and sulfation on reaction of 1,2-dihydroxybenzene and its methyl ethers in concentrated aqueous sulfuric acid," Recl Tray Chim Pays-Bas, 1988, pp. 325-330, vol. 107"

With --CEROFONTAIN et al. "Sulfonation and sulfation on reaction of 1,2-dihydroxybenzene and its methyl ethers in concentrated aqueous sulfuric acid," Recl Trav des Chim Pays-Bas, 1988, pp. 325-330, vol. 107.--

Replace "Davies, "Electroceramics from Source Materials via Molecular Intermediates: BaTIO3 from TIO2 via [TI(catecholate)3]2-," May 1990, J. Am. Ceram, Soc., Aug. 1990, 73(5), 1429-30."

With --Davies, Electroceramics from Source Materials via Molecular Intermediates: $BaTiO_3$ from $TiO_2$ via $[Ti(catecholate)_3]^{2-}$," May 1990, J. Am. Ceram. Soc., 73(5), 1429-30.--

Replace "Davies, "Electroceramics from Source Materials via Molecular Intermediates: PbTIO3 from TIO2 via [Ti(catecholate)3]2-," J. Am. Ceram. Soc., Aug. 1990, 73(8), 2570-2572"

With --Davies, Electroceramics from Source Materials via Molecular Intermediates: $PbTiO_3$ from $TiO_2$ via $[Ti(catecholate)_3]^{2-}$," Aug. 1990, 73(8), 2570-2572.--

Replace "Raymond, "Coordination isomers of biological iron transport compounds. VI. Models of the enterobactin coordination site. A crystal field effect in the structure of potassium tris(catecholato)chromate( III) and - ferrate( III) sesq u ihyd rates, K3[M( 02C6H4)3]. 1 . 5H20, M=chromium, iron," J. Am. Chem. Soc., Mar. 1976, 98(7), 1767-1774."

Signed and Sealed this
Seventeenth Day of March, 2020

Andrei Iancu
*Director of the United States Patent and Trademark Office*

CERTIFICATE OF CORRECTION (continued)
U.S. Pat. No. 10,377,687 B2

With --Raymond, "Coordination Isomers of Biological Iron Transport Compounds. VI. Models of the enterobactin coordination site. A crystal field effect in the structure of potassium tris(catecholato)chromate(III) and - ferrate(III) sesquihydrates, $K_3[M(O_2C_6H_4)_3] \cdot 1.5H_2O$, M = Cr, Fe[1], "J. Am. Chem. Soc., Mar. 1976, 98(7), 1767-1774.--

Replace "Saito et al. "DPPH radical-scavenging reaction of protocatechuic acid: differnce in reactivity between acids and their esters," Hely Chim Acta, 2006, pp. 1395-1407, vol. 89."

With --Saito et al., "DPPH Radical-Scavenging Reaction of Protocatechuic Acid: Difference in Reactivity between Acids and Their Esters, "Helv Chim Acta, 2006, pp. 1395-1407, Vol. 89.--

Replace "Sommer, "Titanium (IV) complexes with ligands having oxygen donor atoms in aqueous solutions," Zeitschrift fur Anorganische and Aligemeine Chemie, Mar. 1963, pp. 191-197, vol. 321, issue 3-4."

With --Sommer, "Titanium (IV) Complexes with Ligands having Oxygen Donor Atoms in Aqueous Solutions," Zeitschrift für Anorganische und Allgemeine Chemie, Mar. 1963, pp. 191-197, vol. 321, issue 3-4."--

Replace "KIM, "Novel catalytic effects of Mn304 for all vanadium redox flow batteries," Chem. Commun., Apr. 2012, 48 (44) , 5455-5457,"

With --KIM, "Novel catalytic effects of $Mn_3O_4$ for all vanadium redox flow batteries," Chem. Commun., Apr. 2012, 48 (44), 5455-5457--